(12) United States Patent
Koshimura et al.

(10) Patent No.: US 11,512,135 B2
(45) Date of Patent: Nov. 29, 2022

(54) METHOD FOR PRODUCING ANTIBODY FUSION PROTEIN

(71) Applicant: JCR Pharmaceuticals Co., Ltd., Hyogo (JP)

(72) Inventors: Yuri Koshimura, Kobe (JP); Hiroyuki Sonoda, Kobe (JP); Miroslav Matev, Kobe (JP); Shinji Kakimoto, Kobe (JP); Tsuyoshi Fukui, Kobe (JP); Yukichi Hatano, Kobe (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 31 days.

(21) Appl. No.: 16/327,982

(22) PCT Filed: Aug. 25, 2017

(86) PCT No.: PCT/JP2017/030470
§ 371 (c)(1),
(2) Date: Feb. 25, 2019

(87) PCT Pub. No.: WO2018/038243
PCT Pub. Date: Mar. 1, 2018

(65) Prior Publication Data
US 2019/0225700 A1    Jul. 25, 2019

(30) Foreign Application Priority Data

Aug. 25, 2016  (JP) .............................. JP2016-164901

(51) Int. Cl.
| | | |
|---|---|---|
| *C07K 16/28* | (2006.01) | |
| *C12N 9/16* | (2006.01) | |
| *C07K 19/00* | (2006.01) | |
| *A61K 47/65* | (2017.01) | |
| *C07K 1/22* | (2006.01) | |
| *C07K 1/36* | (2006.01) | |
| *C07K 16/06* | (2006.01) | |
| *C12N 5/071* | (2010.01) | |
| *C12N 15/09* | (2006.01) | |
| *C12N 5/10* | (2006.01) | |

(52) U.S. Cl.
CPC .......... *C07K 16/2881* (2013.01); *A61K 47/65* (2017.08); *C07K 1/22* (2013.01); *C07K 1/36* (2013.01); *C07K 16/065* (2013.01); *C07K 19/00* (2013.01); *C12N 5/069* (2013.01); *C12N 9/16* (2013.01); *C07K 2317/24* (2013.01); *C07K 2319/00* (2013.01); *C12N 5/10* (2013.01); *C12N 15/09* (2013.01); *C12Y 301/06013* (2013.01)

(58) Field of Classification Search
CPC .......... A61K 47/65; C12N 5/069; C12N 9/18; C12N 9/16; C07K 16/2881; C12Y 301/06013
See application file for complete search history.

(56) References Cited

U.S. PATENT DOCUMENTS

| | | | |
|---|---|---|---|
| 2009/0291473 A1 | 11/2009 | Sugimura et al. | |
| 2011/0110935 A1 | 5/2011 | Pardridge et al. | |
| 2015/0313972 A1 | 11/2015 | Nichols | |
| 2017/0233704 A1 | 8/2017 | Koshimura et al. | |

FOREIGN PATENT DOCUMENTS

| | | |
|---|---|---|
| CN | 1902229 A | 1/2007 |
| CN | 103354837 A | 10/2013 |
| JP | 2009-273427 A | 11/2009 |
| JP | 2010-511378 A | 4/2010 |
| JP | 2012-507550 A | 3/2012 |
| JP | 2013-507131 A | 3/2013 |
| JP | 2014-508506 A | 4/2014 |
| KR | 10-2014-0041443 A | 4/2014 |
| WO | 2005/047307 A2 | 5/2005 |
| WO | 2008/068879 A1 | 6/2008 |
| WO | 2010/051360 A1 | 5/2010 |
| WO | 2011/044542 A1 | 4/2011 |
| WO | 2012/101671 A1 | 8/2012 |
| WO | 2012/101998 A1 | 8/2012 |
| WO | 2014/016873 A1 | 1/2014 |
| WO | 2014/017088 A1 | 1/2014 |
| WO | 2015/098989 A1 | 7/2015 |
| WO | 2016/067944 A1 | 5/2016 |
| WO | 2016/117341 A1 | 7/2016 |

OTHER PUBLICATIONS

Zhou et al., "Brain-penetrating IgG-iduronate 2-sulfatase fusion protein for the mouse," Drug Metabolism and Disposition, 40: 329-335 (2012).
Zhou et al., "Selective plasma pharmacokinetics and brain uptake in the mouse of enzyme fusion proteins derived from species-specific receptor-targeted antibodies," Journal of Drug Targeting, 20: 715-719 (2012).
International Search Report issued in corresponding International Patent Application No. PCT/JP2017/030470 dated Nov. 21, 2017.
International Preliminary Report on Patentability and Written Opinion issued in corresponding International Patent Application No. PCT/JP2017/030470 dated Feb. 26, 2019.

(Continued)

*Primary Examiner* — Ruixiang Li
(74) *Attorney, Agent, or Firm* — Morgan, Lewis & Bockius LLP

(57) ABSTRACT

Disclosed is a method for production of a fusion protein in which an antibody and a lysosomal enzyme are fused. The method comprises; (a) a step of culturing mammalian cells producing the fusion protein in a serum-free medium to let the mammalian cells secrete the fusion protein in the culture medium, (b) a step of collecting culture supernatant by removing the mammalian cells from the culture medium, and (c) a step of purifying the fusion protein from the culture supernatant by using a column chromatography employing as a solid phase a material to which a substance having affinity for the fusion protein has been bound, a column chromatography employing as a solid phase a material having affinity for the phosphate group, and a size exclusion column chromatography.

22 Claims, 2 Drawing Sheets

Specification includes a Sequence Listing.

(56) References Cited

OTHER PUBLICATIONS

Boado et al., "Insulin receptor antibody-iduronate 2-sulfatase fusion protein: pharmacokinetics, anti-drug antibody, and safety pharmacology in Rhesus monkeys," Biotechnology and Bioengineering, 111: 2317-2325 (2014).
Search Report and Written Opinion issued in counterpart Singapore Patent Application No. 11201901495Y dated Feb. 3, 2020.
Extended European Search Report issued in counterpart European Patent Application No. 17843719.0 dated Feb. 17, 2020.
"Accession AZQ78863", NCBI Sequence Revison History, Feb. 2, 2012.
Lu et al., "Expression in CHO Cells and Pharmacokinetics and Brain Uptake in the Rhesus Monkey of an IgG-Iduronate-2-Sulfatase Fusion Protein," Biotechnology and Bioengineering, NIH Public Access Author Manuscript (2012).
"American Heritage Dictionary Entry: wild type", Houghton Mifflin Harcourt Publishing Company, 2020.
Azadeh et al., "A Rapid Two-Step Iduronate-2-Sulfatatse Enzymatic Activity Assay for MPSII Pharmacokinetic Assessment," JIMD Reports, 89-95 (2017).
Sasaki T et al., "IgG H Chain [*Homo sapiens*]", GenBank database, Jul. 17, 2013.
Jin H et al., "immunoglobulin heavy chain, partial [*Homo sapiens*]", GenBank database, Feb. 3, 2014.
Akahori Y et al., "immunoglobulin kappa light chain VLJ region, partial [*Homo sapiens*]", GenBank database, Jul. 26, 2016.
Badarau A et al., "Chain F, Fab Light Chain", GenBank database, Aug. 15, 2016.
Yang X et al., "IGHG1, partial [synthetic construct]", GenBank database, Mar. 19, 2015.
Tachibana H et al., "immunoglobulin light chain, partial [*Homo sapiens*]", GenBank database, Jul. 24, 2016.
Xuejun et al., "Advances in Brain-targeted Drug Delivery Strategies for Protein Polypeptides," Journal of Pharmaceutical Sciences of PLA, 31 (6): 552-556 (2015).
Liu et al., "Recovery and purification process development for monoclonal antibody production," Landes Bioscience, 2(5): 480-499 (2010).
Office Action issued in counterpart European Patent Application No. 17843719.0 dated Nov. 3, 2020.

METHOD FOR PRODUCING ANTIBODY FUSION PROTEIN

SEQUENCE LISTING SUBMISSION VIA EFS-WEB

A computer readable text file, entitled "SequenceListing.txt" created on or about Feb. 25, 2019 with a file size of about 83 kb contains the sequence listing for this application and is hereby incorporated by reference in its entirety.

TECHNICAL FIELD

The present invention relates to a method for producing a fusion protein in which an antibody is fused with a lysosomal enzyme, for example, a method for purifying a recombinant fusion protein, which has been obtained by culturing a host cell into which an expression vector incorporating the gene encoding the fusion protein is introduced, to such a purity as permits its direct use as medical drug.

BACKGROUND ART

Currently, many medicines containing a recombinant protein as an active ingredient are commercially available. Such recombinant proteins are obtained in the culture supernatant by culturing a host cell into which an expression vector incorporating the gene encoding the protein of interest is introduced. The recombinant proteins obtained in the culture supernatant cannot be used as medicines as they are, because they contain contaminants. For using them as medicines, it is necessary to purify the recombinant proteins contained in the culture supernatant.

Reported are methods for purifying the recombinant proteins to such a level as permits their usages as medical drugs, wherein the proteins are obtained in the culture supernatants by culturing the host cells, that host cells are mammalian cells. For example, a method has been reported in which human erythropoietin (hEPO), a glycoprotein that effects on erythroblast progenitor cells to differentiate them into erythrocytes and promotes the production of erythrocytes, is expressed as a recombinant protein using CHO cells as a host cell, and purified from the supernatant by using various kinds of chromatography including dye affinity column chromatography to such a level as permits its use as medical drug (Patent Document 1). Further, for example, a method has been reported in which human follicle stimulating hormone (hFSH), which is one of gonadotropic hormones having the activity to promote the production and secretion of estrogen in the ovary, is expressed as a recombinant protein using CHO cells as a host cell, and purified from the supernatant by using various kinds of chromatography including cation exchange column chromatography to such a level as permits its use as medical drug (Patent Document 2). Further, for example, a method has been reported in which human iduronate-2-sulfatase (hI2S), which is one of lysosome enzymes having the activity of hydrolyzing sulfate bond in glycosaminoglycan (GAG) molecule such as heparan sulfate and dermatan sulfate, is expressed as a recombinant protein using CHO cells as a host cell, and purified from the supernatant by using various kinds of chromatography including cation exchange column chromatography to such a level as permits its use as medical drug (Patent Document 3). And, for example, human α-galactosidase A (ha-Gal A), which is one of lysosome enzymes having the activity of hydrolyzing terminal α-galactosyl bonds of glycolipids and glycoproteins, is expressed as a recombinant protein using CHO cells as a host cell, and purified from the supernatant by using various kinds of chromatography including anion exchange column chromatography to such a level as permits its use as medical drug (Patent Document 4 and 5). Further, for example, human DNase I, having the activity of degrading DNA nonspecifically in a base sequence, is expressed as a recombinant protein using CHO cells as a host cell, and purified from the supernatant by using various kinds of chromatography including dye ligand affinity column chromatography to such a level as permits its use as medical drug (Patent Document 6).

As such in order to obtain a recombinant protein that can be used as a medicine, unique purification methods have been developed for each one of recombinant proteins.

CITATION LIST

Patent Literature

[Patent Document 1] JP 2010-511378
[Patent Document 2] JP 2009-273427
[Patent Document 3] JP 2014-508506
[Patent Document 4] WO 2014/017088
[Patent Document 5] WO 2016/117341
[Patent Document 6] WO 2016/067944

SUMMARY OF INVENTION

Technical Problem

An objective of the present invention is to provide a method for expressing a fusion protein in which an antibody is fused to another protein as a recombinant protein, and purifying the protein to such a purity as permits its distribution to the market as a medical drug.

Solution to Problem

In a study for the above-mentioned object, as a result of intense studies, the present inventors found that a fusion protein, in which an anti-transferrin receptor antibody has been fused to human iduronate-2-sulfatase (hI2S), can be purified effectively and at high purity by culturing in a serum-free medium mammalian cells introduced with the expression vector incorporated a gene encoding the fusion protein, and purifying the fusion protein obtained in the culture supernatant by using by using a column chromatography employing as a solid phase a material having affinity for the fusion protein, a column chromatography employing as a solid phase a material having affinity for the phosphate group, and a size exclusion column chromatography. The present invention was completed based on these findings. Thus the present invention provides what follows:

1. A method for production of a fusion protein in which an antibody and a human lysosomal enzyme are fused, the method comprising;
   (a) a step of culturing mammalian cells producing the fusion protein in a serum-free medium to let the mammalian cells secrete the fusion protein in the culture medium,
   (b) a step of collecting culture supernatant by removing the mammalian cells from the culture medium, and
   (c) a step of purifying the fusion protein from the culture supernatant by a column chromatography employing as a solid phase a material to which a substance having affinity for the fusion protein has been bound, a column chromatography employing as a solid phase a material having affinity for the phosphate group, and a size exclusion column chromatography.

2. The method for production according to (1) above, wherein, in the step (c), the column chromatography employing as a solid phase a material to which a substance having affinity for the fusion protein has been bound, the column chromatography employing as a solid phase a material having affinity for the phosphate group, and the size exclusion column chromatography are conducted in this order.

3. The method for production according to (1) or (2) above, wherein the substance having affinity for the fusion protein is selected from the group consisting of Protein A, Protein G, Protein L, Protein A/G, an antigen against said antibody, an antibody recognizing said antibody as an antigen, and an antibody against the lysosomal enzyme.

4. The method for production according to any one of (1) to (3) above, wherein the material having affinity for a phosphate group is fluoroapatite or hydroxyapatite.

5. The method for production according to any one of (1) to (3) above, wherein the material having affinity for phosphate group is hydroxyapatite.

6. The method for production according to any one of (1) to (5) above, wherein said antibody fused to the human lysosomal enzyme is a humanized antibody or a human antibody.

7. The method for production according to any one of (1) to (5) above, wherein said antibody fused to the human lysosomal enzyme is a humanized antibody.

8. The method for production according to any one of (1) to (7) above, wherein said antibody fused to the human lysosomal enzyme recognizes a molecule present on the surface of vascular endothelial cells as an antigen.

9. The method for production according to (8) above, wherein the molecule present on the surface of vascular endothelial cells is selected from the group consisting of transferrin receptor (TfR), insulin receptor, leptin receptor, lipoprotein receptor, IGF receptor, OATP-F, organic anion transporter, MCT-8, monocarboxylic acid transporter, and an Fc receptor.

10. The method for production according to (8) above, wherein the vascular endothelial cells are cerebral vascular endothelial cells.

11. The method for production according to (10) above, wherein the molecule present on the surface of the cerebrovascular endothelial cell is selected from the group consisting of transferrin receptor (TfR), insulin receptor, leptin receptor, lipoprotein receptor, IGF receptor, OATP-F, organic anion transporter, MCT-8, and monocarboxylic acid transporter.

12. The method for production according to any one of (8) to (11) above, wherein the vascular endothelial cells are human vascular endothelial cells.

13. The method for production according to any one of (1) to (12) above, wherein said antibody is an anti-human transferrin receptor antibody.

14. The method for production according to any one of (1) to (13) above, wherein said antibody and the human lysosomal enzyme are fused via a linker in the fusion protein, and wherein the linker is selected from the group consisting of polyethylene glycol, polypropylene glycol, copolymer of ethylene glycol and propylene glycol, polyoxyethylated polyol, polyvinyl alcohol, polysaccharide, dextran, polyvinyl ether, biodegradable polymer, lipid polymer, chitin, hyaluronic acid, biotin-streptavidin, and a derivative thereof.

15. The method for production according to any one of (1) to (13) above, wherein the human lysosomal enzyme is linked, by peptide bonds directly or via a linker sequence, to the heavy chain of said antibody on the C-terminal side or the N-terminal side thereof in the fusion protein.

16. The method for production according to any one of (1) to (13) above, wherein the human lysosomal enzyme is linked, by peptide bonds directly or via a linker sequence, to the light chain of said antibody on the C-terminal side or the N-terminal side thereof in the fusion protein.

17. The method for production according to (15) or (16) above, wherein the linker sequence consists of 1 to 50 amino acid residues.

18. The method for production according to (17), wherein the linker sequence comprises an amino acid sequence selected from the group consisting of a single glycine, a single serine, the amino acid sequence of Gly-Ser, the amino acid sequence of Gly-Gly-Ser, the amino acid sequence set forth as SEQ ID NO:1, the amino acid sequence set forth as SEQ ID NO:2, the amino acid sequence set forth as SEQ ID NO:3, and the amino acid sequences consisting of 1 to 10 thereof that are consecutively linked.

19. The method for production according to (17) or (18) above, wherein the linker sequence is represented by the amino acid sequence of Gly-Ser.

20. The method for production according to any one of (1) to (19) above, wherein the human lysosomal enzyme is human iduronate-2-sulfatase (human I2S).

21. The method for production according to (20) above, wherein the human I2S comprises the amino acid sequence set forth as SEQ ID NO:5.

22. The method for production according to (20) above, wherein the human I2S has at least 80% amino acid sequence identity to the amino acid sequence set forth as SEQ ID NO:5, and has an activity as human I2S.

23. The method for production according to (20) above, wherein the human I2S has at least 90% amino acid sequence identity to the amino acid sequence set forth as SEQ ID NO:5, and has an activity as human I2S.

24. The method for production according to (20) above, wherein the human I2S has the amino acid sequence introduced 1 to 10 amino acid substitutions, deletions or additions relative to the amino acid sequence set forth as SEQ ID NO:5, and has an activity as human I2S.

25. The method for production according to (20) above, wherein the human I2S has the amino acid sequence introduced 1 to 5 amino acid substitutions, deletions or additions relative to the amino acid sequence set forth as SEQ ID NO:5, and has an activity as human I2S.

26. The method for production according to (20) above, wherein the human I2S has the amino acid sequence introduced 1 to 3 amino acid substitutions, deletions or additions relative to the amino acid sequence set forth as SEQ ID NO:5, and has an activity as human I2S.

27. The method for production according to any one of (1) to (26) above, wherein said antibody is a human anti-hTfR antibody, and the human anti-hTfR antibody is selected from the group consisting of (a) to (c) below;

(a) the human anti-hTfR antibody, wherein the light chain and the heavy chain thereof comprise the amino acid sequences set forth as SEQ ID NO:6 and SEQ ID NO:7, respectively, (b) the human anti-hTfR antibody, wherein the light chain and the heavy chain thereof comprise the amino acid sequences set forth as SEQ ID NO:8 and SEQ ID NO:9, respectively, and (c) the human anti-hTfR antibody, wherein the light chain and the heavy chain thereof comprise the amino acid sequences set forth as SEQ ID NO: 10 and SEQ ID NO: 11, respectively.

28. The method for production according to any one of (1) to (26) above, wherein said antibody is a human anti-hTfR antibody, and the human anti-hTfR antibody is selected from the group consisting of (a) to (c) below;
(a) the human anti-hTfR antibody, wherein the light chain and the heavy chain thereof have at least 80% amino acid sequence identity to the amino acid sequence set forth as SEQ ID NO:6 and SEQ ID NO:7, respectively,
(b) the human anti-hTfR antibody, wherein the light chain and the heavy chain thereof have at least 80% amino acid sequence identity to the amino acid sequence set forth as SEQ ID NO:8 and SEQ ID NO:9, respectively, and
(c) the human anti-hTfR antibody, wherein the light chain and the heavy chain thereof have at least 80% amino acid sequence identity to the amino acid sequence set forth as SEQ ID NO:10 and SEQ ID NO: 11, respectively.

29. The method for production according to any one of (1) to (26) above, wherein said antibody is a human anti-hTfR antibody, and the human anti-hTfR antibody is selected from the group consisting of (a) to (c) below;
(a) the human anti-hTfR antibody, wherein the light chain and the heavy chain thereof have at least 90% amino acid sequence identity to the amino acid sequence set forth as SEQ ID NO:6 and SEQ ID NO:7, respectively,
(b) the human anti-hTfR antibody, wherein the light chain and the heavy chain thereof have at least 90% amino acid sequence identity to the amino acid sequence set forth as SEQ ID NO:8 and SEQ ID NO:9, respectively, and
(c) the human anti-hTfR antibody, wherein the light chain and the heavy chain thereof have at least 90% amino acid sequence identity to the amino acid sequence set forth as SEQ ID NO:10 and SEQ ID NO: 11, respectively.

30. The method for production according to any one of (1) to (26) above, wherein said antibody is a human anti-hTfR antibody, and the human anti-hTfR antibody is selected from the group consisting of (a) to (c) below;
(a) the human anti-hTfR antibody, wherein the light chain thereof has the amino acid sequence introduced 1 to 10 amino acid substitutions, deletions or additions relative to the amino acid sequence set forth as SEQ ID NO:6, and wherein the heavy chain thereof has the amino acid sequence introduced 1 to 10 amino acid substitutions, deletions or additions relative to the amino acid sequence set forth as SEQ ID NO:7,
(b) the human anti-hTfR antibody, wherein the light chain thereof has the amino acid sequence introduced 1 to 10 amino acid substitutions, deletions or additions relative to the amino acid sequence set forth as SEQ ID NO:8, and wherein the heavy chain thereof has the amino acid sequence introduced 1 to 10 amino acid substitutions, deletions or additions relative to the amino acid sequence set forth as SEQ ID NO:9, and
(c) the human anti-hTfR antibody, wherein the light chain thereof has the amino acid sequence introduced 1 to 10 amino acid substitutions, deletions or additions relative to the amino acid sequence set forth as SEQ ID NO:10, and wherein the heavy chain thereof has the amino acid sequence introduced 1 to 10 amino acid substitutions, deletions or additions relative to the amino acid sequence set forth as SEQ ID NO: 11.

31. The method for production according to any one of (1) to (26) above, wherein said antibody is a human anti-hTfR antibody, and the human anti-hTfR antibody is selected from the group consisting of (a) to (c) below;
(a) the human anti-hTfR antibody, wherein the light chain thereof has the amino acid sequence introduced 1 to 3 amino acid substitutions, deletions or additions relative to the amino acid sequence set forth as SEQ ID NO:6, and wherein the heavy chain thereof has the amino acid sequence introduced 1 to 3 amino acid substitutions, deletions or additions relative to the amino acid sequence set forth as SEQ ID NO:7,
(b) the human anti-hTfR antibody, wherein the light chain thereof has the amino acid sequence introduced 1 to 3 amino acid substitutions, deletions or additions relative to the amino acid sequence set forth as SEQ ID NO:8, and wherein the heavy chain thereof has the amino acid sequence introduced 1 to 3 amino acid substitutions, deletions or additions relative to the amino acid sequence set forth as SEQ ID NO:9, and
(c) the human anti-hTfR antibody, wherein the light chain thereof has the amino acid sequence introduced 1 to 3 amino acid substitutions, deletions or additions relative to the amino acid sequence set forth as SEQ ID NO:10, and wherein the heavy chain thereof has the amino acid sequence introduced 1 to 3 amino acid substitutions, deletions or additions relative to the amino acid sequence set forth as SEQ ID NO:11.

32. The method for production according to (20) above, wherein said antibody is a human anti-hTfR antibody, the human lysosomal enzyme is human iduronate-2-sulfatase, and the fusion protein is selected from the group consisting of (a) to (c) below;
(a) the fusion protein comprising the light chain of the humanized anti-hTfR antibody having the amino acid sequence set forth as SEQ ID NO:6, and the heavy chain of the humanized anti-hTfR antibody having the amino acid sequence set forth as SEQ ID NO:12 to which the human iduronate-2-sulfatase set forth as SEQ ID NO:1 is linked on the C-terminal side thereof and via a linker sequence of Gly-Ser,
(b) the fusion protein comprising the light chain of the humanized anti-hTfR antibody having the amino acid sequence set forth as SEQ ID NO:8, and the heavy chain of the humanized anti-hTfR antibody having the amino acid sequence set forth as SEQ ID NO:13 to which the human iduronate-2-sulfatase set forth as SEQ ID NO:1 is linked on the C-terminal side thereof and via a linker sequence of Gly-Ser, and
(c) the fusion protein comprising the light chain of the humanized anti-hTfR antibody having the amino acid sequence set forth as SEQ ID NO:10, and the heavy chain of the humanized anti-hTfR antibody having the amino acid sequence set forth as SEQ ID NO:14 to which the human iduronate-2-sulfatase set forth as SEQ ID NO:1 is linked on the C-terminal side thereof and via a linker sequence of Gly-Ser.

33. The method for production according to (20) above, wherein said antibody is a human anti-hTfR antibody, the human lysosomal enzyme is human iduronate-2-sulfatase (human I2S), and the fusion protein is selected from the group consisting of (a) to (c) below;
(a) the fusion protein comprising;
the light chain of the humanized anti-hTfR antibody having the amino acid sequence set forth as SEQ ID NO:6, and
the heavy chain of the humanized anti-hTfR antibody to which the human iduronate-2-sulfatase is linked on the C-terminal side thereof via a linker sequence of Gly-Ser, and having the amino acid sequence set forth as SEQ ID NO: 12 as a whole,
(b) the fusion protein comprising;
the light chain of the humanized anti-hTfR antibody having the amino acid sequence set forth as SEQ ID NO:8, and
the heavy chain of the humanized anti-hTfR antibody to which the human iduronate-2-sulfatase is linked on the C-terminal side thereof via a linker sequence of Gly-Ser, and having the amino acid sequence set forth as SEQ ID NO:13 as a whole, and
(c) the fusion protein comprising;
the light chain of the humanized anti-hTfR antibody having the amino acid sequence set forth as SEQ ID NO:10, and
the heavy chain of the humanized anti-hTfR antibody to which the human iduronate-2-sulfatase is linked on the C-terminal side thereof via a linker sequence of Gly-Ser, and having the amino acid sequence set forth as SEQ ID NO:14 as a whole.

Effects of Invention

The present invention enables to provide a fusion protein of an anti-transferrin receptor antibody and a lysosomal enzyme, that fusion protein has been purified to such a purity as permits its clinical usage as a therapeutic agent for a lysosomal disease accompanied with central nervous system disorders. In particular, it enables to provide a fusion protein of anti-transferrin receptor antibody and human I2S purified to such a purity as permits its clinical usage as a therapeutic agent for Hunter syndrome accompanied with central nervous system disorders.

DESCRIPTION OF EMBODIMENTS

Figure 1:
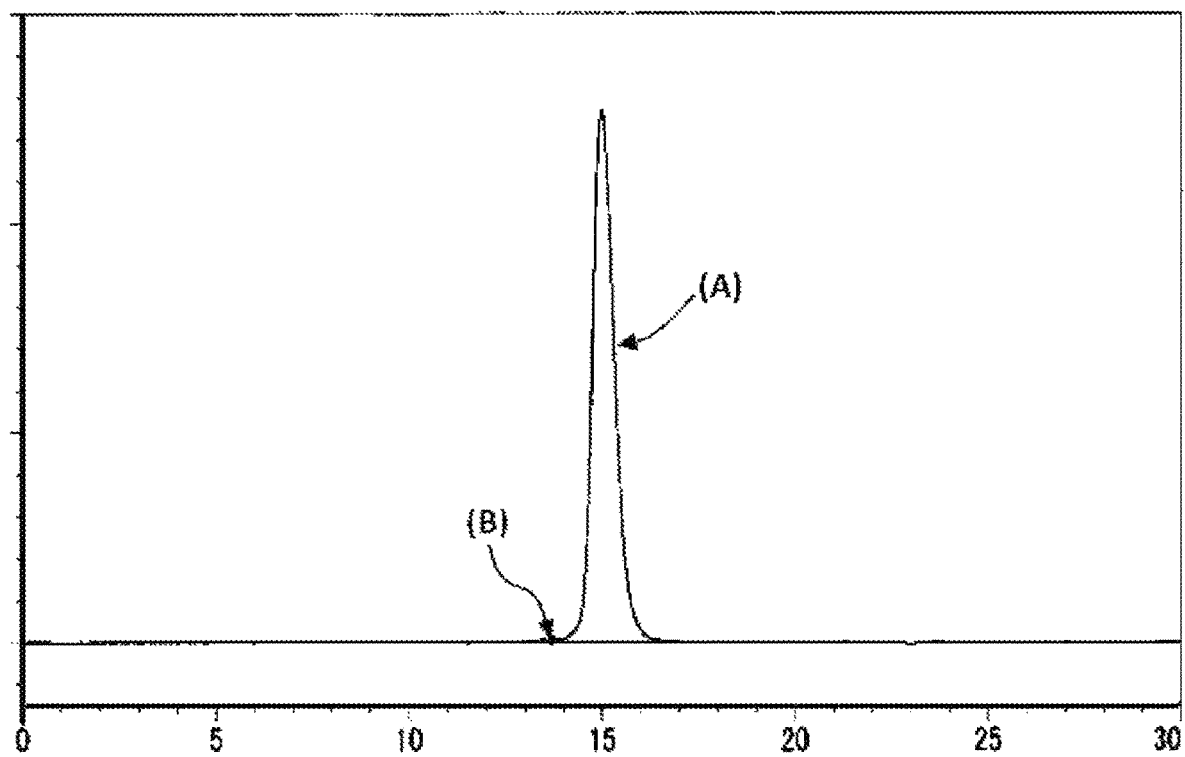
FIG. 1 shows the SE-HPLC chart of the purified product of I2S-anti-hTfR antibody obtained in Example 6. The vertical axis shows absorbance at 215 nm, and the horizontal axis shows retention time. (A): a peak corresponding to monomer of I2S-anti-hTfR antibody 3, (B): a peak corresponding to multimer of I2S-anti-hTfR antibody 3.

The present invention relates to a method for producing a protein in which an anti-transferrin receptor antibody (anti-TfR antibody) is bound to a human lysosomal enzyme. Here, the antibody to be bound to the lysosomal enzyme is not particularly limited as to the animal species of the antibody, as long as it has a property to specifically bind to the antigen, but particularly, it is a human antibody or a humanized antibody. For example, the antibody may be an antibody of a mammal other than human, or it may be a chimeric antibody of a human antibody and a mammalian antibody other than human.

The term "human antibody" refers to an antibody whose entirety is encoded by a gene originating from human. However, the term "human antibody", however, also includes an antibody encoded by a gene obtained by introducing a mutation into an original human gene for a purpose of enhancing expression efficiency of the gene, for example, without modifying the original amino acid sequence. The term "human antibody" also includes an antibody which is produced by combining two or more genes encoding human antibodies and replacing a certain part of a human antibody with a part of another human antibody. A human antibody includes three complementarity determining regions (CDRs) in the light chain of the immunoglobulin and three complementarity determining regions (CDRs) in the heavy chain of the immunoglobulin. The three CDRs in the light chain of the immunoglobulin are called, from the N-terminal side, CDR1, CDR2 and CDR3, respectively. The three CDRs in the heavy chain of the immunoglobulin are also called, from the N-terminal side, CDR1, CDR2 and CDR3, respectively. The term "human antibody" also includes human antibody produced by replacing a CDR of a human antibody with a CDR of another human antibody to modify such properties as the antigen specificity and the affinity of the original human antibodies, etc.

In the present invention, the term "human antibody" also includes an antibody which is produced through modification of the gene of the original human antibody by introducing a mutation, such as substitution, deletion, addition, to the amino acid sequence of the original antibody. When replacing one or more amino acids of the amino acid sequence of the original antibody with other amino acids, the number of amino acid replaced may preferably be 1 to 20, more preferably 1 to 10, still more preferably 1 to 5, and still more preferably 1 to 3. When deleting one or more amino acids of the amino acid sequence of the original antibody, the number of amino acids deleted may preferably be 1 to 20, more preferably 1 to 10, still more preferably 1 to 5, and still more preferably 1 to 3. An antibody produced by a combined mutation of these substitution and deletion of amino acids is also a "human antibody". In some cases, one or more amino acids, preferably 1 to 20, more preferably 1 to 10, still more preferably 1 to 5, and still more preferably 1 to 3 amino acids may be added inside the amino acid sequence of the original antibody or on its N- or C-terminus. An antibody produced by a combined mutation of addition, substitution, and deletion of amino acids is also a "human antibody". The amino acid sequence of such a mutated antibody has an identity of preferably not lower than 80%, more preferably not lower than 90%, still more preferably not lower than 95%, and even more preferably not lower than 98%, to the amino acid sequence of the original antibody. Thus, in the present invention, the term "gene originating from human" includes not only the unmutated gene originating from human but also a gene produced by modifying it.

In the present invention, the term "humanized antibody" refers to an antibody in which part of the amino acid sequence of its variable region (e.g., especially the whole or part of its CDRs) originates from a non-human mammal while the rest originates from human. An example of humanized antibody is an antibody produced by replacing the three complementarity determining regions (CDRs) of the light chain of the immunoglobulin and the three complementarity determining regions (CDRs) of the heavy chain of the immunoglobulin constituting a human antibody, with CDRs from a non-human mammal. As far as it originates from a non-human mammal, there is no particular limitation as to the biological species from which those CDRs originate that are grafted into a proper position of the human antibody, though preferred are mouse, rat, rabbit, horse or non-human primate, for example mouse.

A detailed explanation will be given below regarding the case where the antibody is a humanized antibody or human antibody. In human antibody light chain, there are λ and κ chains. The light chain constituting the antibody may either be λ and κ chain. And in heavy chain of human or humanized antibody, there are γ, μ, α, σ, and ε chains, which correspond to IgC; IgM, IgA, IgD and IgE, respectively. Though the heavy chain constituting the antibody may be any of γ, μ, α, σ, and ε chains, preferred is a γ chain. Further, in γ chain of antibody heavy chain, there are γ1, γ2, γ3 and γ4 chains, which correspond to IgG1, IgG2, IgG3 and IgG4, respectively. Where the heavy chain constituting the antibody is a γ chain, though the γ chain may be any of γ1, γ2, γ3 and γ4 chains, preferred is a γ1 or γ4 chain. In the case where the antibody is a humanized antibody or human antibody and IgG, the antibody light chain may either be λ chain or κ chain, and though the antibody heavy chain may either be γ1, γ2, γ3 and γ4 chains, preferred is a γ1 or γ4 chain. For example, a preferable embodiment of the antibody includes an antibody whose light chain is a λ chain and heavy chain is a γ1 chain.

In the present invention, the term "chimeric antibody" refers to an antibody produced by connecting fragments of two or more different antibodies originating from two or more different species.

A chimeric antibody between a human antibody and a non-human mammalian antibody is an antibody provided by replacing part of a human antibody with part of a non-human mammalian antibody. As explained below, an antibody is made of an Fc region, a Fab region and a hinge region. A specific example of such chimeric antibodies is a chimeric antibody whose Fc region originates from a human antibody while its Fab region originates from a non-human mammalian antibody. The hinge region either originates from a human antibody or from a non-human mammalian antibody. On the contrary, the term chimeric antibody also includes one whose Fc region originates from a non-human mammalian antibody while its Fab region originates from a human antibody. In such a case also, the hinge region either originates from a human antibody or from a non-human mammalian antibody.

An antibody can be viewed as composed of a variable region and a constant region. Additional examples of chimeric antibodies include an antibody in which the heavy chain constant region ($C_H$) and the light chain constant region ($C_1$) both originate from a human antibody while the heavy chain variable region ($V_H$) and the light chain variable region ($V_L$) both originate from an antibody of a non-human mammal, and conversely, an antibody in which the heavy chain constant region ($C_H$) and the light chain constant region ($C_1$) both originate from an antibody of a non-human mammal, while the heavy chain variable region ($V_H$) and the light chain variable region ($V_L$) both originate from a human antibody. In these, there is no particular limitation as to the biological species of the non-human mammal, as far as it is a non-human mammal, though preferred are mouse, rat, rabbit, horse or non-human primate, and mouse, more preferably mouse.

A chimeric antibody between a human antibody and a mouse antibody is designated in particular "human/mouse chimeric antibody". Examples of human/mouse chimeric antibodies include a chimeric antibody in which the Fc region originates from a human antibody while the Fab region originates from a mouse antibody, and conversely, a chimeric antibody whose Fc region originates from mouse antibody, while its Fab region originates from a human antibody. A hinge region either originate from a human antibody or a mouse antibody. Additional specific examples of human/mouse chimeric antibodies include those whose heavy chain constant region ($C_H$) and light chain constant region ($C_1$) originate from a human antibody while its heavy chain variable region ($V_H$) and light chain variable region ($V_L$) originate from a mouse antibody, and conversely, those whose heavy chain constant region ($C_H$) and light chain constant region ($C_1$) originate from a mouse antibody while its heavy chain variable region ($V_H$) and light chain variable region ($V_L$) originate from a human antibody.

Originally, an antibody is of the basic structure having four polypeptide chains in total consisting of two immunoglobulin light chains and two immunoglobulin heavy chains. However, in the present invention the term "antibody" refers, besides an antibody having this basic structure, also to:

(1) one consisting of two polypeptide chains: a single immunoglobulin light chain and a single immunoglobulin heavy chain, and also, as explained later, (2) a single-chain antibody consisting of an immunoglobulin light chain which is linked, on the C-terminal side thereof, to a linker sequence which in turn is linked, on the C-terminal side thereof, to an immunoglobulin heavy chain, (3) single-chain antibodies consisting of an immunoglobulin heavy chain which is linked, on the C-terminal side thereof, to a linker sequence which in turn is linked, on the C-terminal side thereof, to an immunoglobulin light chain, and (4) one consisting of a Fab region, i.e., a structure left behind by removal of the Fc region from an antibody having the basic structure, as the original meaning, and one consisting of the Fab region and the whole or part of the hinge region (including Fab, F(ab'), and F(ab')$_2$) also are included in the term "antibody" in the present invention. Furthermore, scFv in which the variable region of the light chain and the variable region of the heavy chain are linked via a linker sequence to form a single chain antibody is also included in the antibody of the present invention.

In the present invention, the term "single-chain antibody" refers to a protein in which an amino acid sequence comprising the whole or part of an immunoglobulin light chain variable region linked, on the C-terminal side thereof, to a linker sequence, which in turn is linked, on the C-terminal side thereof, to the amino acid sequence of the whole or part of an immunoglobulin heavy chain variable region, and having an ability to specifically bind a certain antigen. Further, a protein in which an amino acid sequence comprising the whole or part of an immunoglobulin heavy chain variable region is linked, on the C-terminal side thereof, to a linker sequence, which in turn is further linked, on the C-terminal side thereof, to the amino acid sequence of the whole or part of an immunoglobulin light chain variable region, and which has an ability to specifically bind to a certain antigen, is also included in the term "single-chain antibody" in the present invention. For example, those described in (2) and (3) are included in "single-chain antibody". In a single-chain antibody in which an immunoglobulin heavy chain is linked, on the C-terminal side thereof and via a linker sequence, to an immunoglobulin light chain, the immunoglobulin heavy chain generally lacks the Fc region. An immunoglobulin light chain variable region has three complementarity determining regions (CDRs) which participate in determining the antigen specificity of an antibody. Likewise, an immunoglobulin heavy chain variable region also has three CDRs. Those CDRs are the primary regions that determine the antigen specificity of an antibody. Therefore, a single-chain antibody preferably contains all the three CDRs of the immunoglobulin heavy chain and all the three CDRs of the immunoglobulin light chain. However, it is also possible to provide a single-chain antibody in which one or more of those CDRs are deleted, insofar as the antigen-specific affinity of the antibody is retained.

In a single-chain antibody, the linker sequence placed between the light chain and the heavy chain of the immunoglobulin is preferably a peptide chain consisting of preferably 2 to 50, more preferably 8 to 50, still more preferably 10 to 30, even more preferably 12 to 18, or 15 to 25, for example 15 or 25 amino acid residues. While there is no particular limitation as to the specific amino acid sequence of such a linker sequence insofar as the anti-hTfR antibody comprising the both chains linked thereby retains the affinity to hTfR, it is preferably made of glycine only, or of glycine and serine. For example, there are the amino acid sequence Gly-Ser, the amino acid sequence of Gly-Gly-Ser, the amino acid sequence of Gly-Gly-Gly, the amino acid sequence of Gly-Gly-Gly-Gly-Ser (SEQ ID NO:1), the amino acid sequence of Gly-Gly-Gly-Gly-Gly-Ser (SEQ ID NO:2), the amino acid sequence of Ser-Gly-Gly-Gly-Gly-Gly (SEQ ID NO:3), or a sequence which includes a sequence corresponding to 2 to 10 or 2 to 5 of any of those amino acid sequences consecutively linked. For example, in linking the amino acid sequence of the entire immunoglobulin heavy chain variable region on the C-terminal side thereof and via a linker sequence, to immunoglobulin light chain variable region to produce ScFV a preferable linker sequence comprises a linker sequence consisting of a total of 15 amino acids corresponding to three of the amino acid sequence of Gly-Gly-Gly-Gly-Ser (SEQ ID NO:1) consecutively linked.

In the present invention, the antigen specifically recognized by the antibody is, for example, a molecule present on the surface of vascular endothelial cells (surface antigen). Examples of such surface antigens include transferrin receptor (TfR), insulin receptor, leptin receptor, lipoprotein receptor, IGF receptor, organic anion transporters such as OATP-F, monocarboxylic acid transporters such as MCT-8, Fc receptors, and the like, but are not limited to these. Antigens are preferably these molecules (surface antigens) present on the surface of human vascular endothelial cells.

Among the surface antigens described above, organic anion transporters such as transferrin receptor (TfR), insulin receptor, leptin receptor, lipoprotein receptor, IGF receptor, OATP-F and the like, monocarboxylic acid transduct such as MCT-8 Porter is present on the surface of brain capillary endothelial cells (cerebral vascular endothelial cells) forming the blood brain barrier (Blood Brain Barrier). Antibodies capable of recognizing these antigens can bind to brain capillary endothelial cells via antigens. And antibodies bound to brain capillary endothelial cells can cross the blood brain barrier and reach the central nervous system. Therefore, by binding the protein of interest to such an antibody, it is possible to reach the central nervous system. Protein of interest may be a protein having a function to exert a drug effect in the central nervous system. For example, lysosomal enzymes that are deficient or dysfunctional in lysosomal disease patients with central nervous system disorders are mentioned as proteins of interest. Such a lysosomal enzyme cannot reach the central nervous system as it is and does not show a drug effect against a central nervous system disorder of a patient, but by allowing it to bind with these antibodies, it can pass through the blood brain barrier As a result, the central nervous system disorder found in lysosomal disease patients can be improved.

In the present invention, the term "human transferrin receptor" or "hTfR" refers to a membrane protein having the amino acid sequence set forth as SEQ ID NO:4. The anti-hTfR antibody of the present invention is, in one of its embodiments, that which binds also to the region from the cysteine residue at the position 89th from the N-terminus to the phenylalanine at the C-terminus in the amino acid sequence set forth as SEQ ID NO:4 (i.e., the extracellular region of the monkey TfR), though it is not limited to this embodiment.

A method for preparing an antibody is described below, an antibody against hTfR taken as an example. For preparation of an antibody to hTtR, there is known a general method according to which a recombinant human transferrin receptor (rhTfR) is produced using cells which have an introduced expression vector having an incorporated hTfR gene, and then animals such as mice are immunized with this rhTfR. By collecting those cells which produce antibodies to hTfR from the immunized animals and fusing them with myeloma cells, hybridoma cells can be obtained having an ability to produce the anti-hTfR antibody.

Further, cells producing an antibody to hTfR can also be obtained by collecting immunocompetent cells from an animal such as mouse, and immunizing them with rhTfR by in vitro immunization. In conducting immunization by vitro immunization, there is no particular limitation as to the animal species from which the immunocompetent cells are derived, though preferred are mouse, rat, rabbit, guinea pig, dog, cat, horse, and primates including human, and more preferred are mouse, rat and human, and still more preferably mouse and human. As mouse immunocompetent cells, spleen cells prepared from mouse spleen may be used, for example. As human immunocompetent cells, such cells can be used as prepared from human peripheral blood, bone marrow, spleen, and the like. By immunizing human immunocompetent cells according to in vitro immunization, a human antibody to hTfR can be obtained.

In the present invention, there is no particular limitation as to the human lysosomal enzyme to be linked to the anti-hTfR antibody. As such lysosomal enzymes, included are α-L-iduronidase, iduronate-2-sulfatase, glucocerebrosidase, β-galactosidase, GM2 activator protein, β-hexosaminidase A, β-hexosaminidase B, N-acetylglucosamine-1-phosphotransferase, α-mannosidase, β-mannosidase, galactosylceramidase, saposin C, arylsulfatase A, α-L-fucosidase, aspartylglucosaminidase, α-N-acetylgalactosaminidase, acidic sphingomyelinase, α-galactosidase A, β-glucuronidase, heparan N-sulfatase, α-N-acetylglucosaminidase, acetyl CoA:α-glucosaminide N-acetyltransferase, N-acetylglucosamine-6-sulfate sulfatase, acid ceramidase, amylo-1,6-glucosidase, sialidase, aspartylglucosaminidase (PPT1), tripeptidyl-peptidase 1 (TPP-1), hyaluronidase 1, CLN1, and CLN2, and the like.

When the antibody specifically recognizes a molecule present on the surface of the vascular endothelial cell (surface antigen), the human lysosomal enzyme linked to the antibody can be used as a therapeutic agent for central nervous system disorders, i.e. α-L-iduronidase as a therapeutic agent for central nervous system disorders in Hurler syndrome or Hurler-Scheie syndrome; iduronate-2-sulfatase as a therapeutic agent for central nervous system disorders in Hunter syndrome; glucocerebrosidase as a therapeutic agent for central nervous system disorders in Gaucher's disease; β-galactosidase as a therapeutic agent for central nervous system disorders in GM1 gangliosidosis Types 1 to 3; GM2 activator protein as a therapeutic agent for central nervous system disorders in GM2-gangliosidosis, AB variant; β-hexosaminidase A as a therapeutic agent for central nervous system disorders in Sandhoff's disease and Tay-Sachs disease; β-hexosaminidase B as a therapeutic agent for central nervous system disorders in Sandhoff's disease; N-acetylglucosamine-1-phosphotransferase as a therapeutic agent for central nervous system disorders in I-cell disease; α-mannosidase as a therapeutic agent for central nervous system disorders in α-mannosidosis; β-mannosidase as a therapeutic agent for central nervous system disorders in β-mannosidosis; galactosylceramidase as a therapeutic agent for central nervous system disorders in Krabbe disease; saposin C as a therapeutic agent for central nervous system disorders in Gaucher's disease-like storage disease; arylsulfatase A as a therapeutic agent for central nervous system disorders in metachromatic white matter degeneration (metachromatic leukodystrophy); α-L-fucosidase as a therapeutic agent for central nervous system disorders in fucosidosis; aspartylglucosaminidase as a therapeutic agent for central nervous system disorders in aspartylglucosaminuria; α-N-acetylgalactosaminidase as a therapeutic agent for central nervous system disorders in Schindler disease and Kawasaki disease; acidic sphingomyelinase as a therapeutic agent for central nervous system disorders in Niemann-Pick disease; α-galactosidase A as a therapeutic agent for central nervous system disorders in Fabry disease; β-glucuronidase as a therapeutic agent for central nervous system disorders in Sly syndrome; heparan N-sulfatase, α-N-acetylglucosaminidase, acetyl CoA:α-glucosaminide N-acetyltransferase and N-acetylglucosamine-6-sulfate sulfatase as therapeutic agents for central nervous system disorders in Sanfilippo syndrome; acid ceramidase as a therapeutic agent for central nervous system disorders in Farber disease; amylo-1,6-glucosidase as a therapeutic agent for central nervous system disorders in Cori's disease (Forbes-Cori's disease); sialidase as a therapeutic agent for central nervous system disorders in sialidase deficiency; aspartylglucosaminidase as a therapeutic agent for central nervous system disorders in aspartylglucosaminuria; palmitoyl protein thioesterase 1 (PPT-1) as a therapeutic agent for central nervous system disorders in neuronal ceroid lipofuscinosis or Santavuori-Haltia disease; tripeptidyl-peptidase 1 (TPP-1) as a therapeutic agent for central nervous system disorders in neuronal ceroid lipofuscinosis or Jansky-Bielschowsky disease; hyaluronidase 1 as a therapeutic agent for central nervous system disorders in hyaluronidase deficiency; CLN1 and CLN2 as therapeutic agents for central nervous system disorders in Batten disease. In particular, the anti-hTfR antibody of the present invention, after passing through the blood-brain barrier, reaches the brain parenchyma and the hippocampus neuron-like cells of the cerebrum, and Purkinje cells of the cerebellum, and is expected further to reach neuron-like cells of the striatum of the cerebrum and the neuron-like cells of the substantia nigra of the mesencephalon. Therefore, the anti-hTfR antibody can be fused with proteins which need to exhibit their functions in those tissues or cells to strength the pharmacological effects of the proteins. Medical applications of it, however, are not limited thereto.

In the case where the antibody specifically recognizes a molecule present on the surface of vascular endothelial cells (surface antigen), lysosomal enzymes to be preferably linked to the antibody include human iduronate-2-sulfatase (hI2S). I2S is one of lysosome enzyme having an activity for hydrolyzing sulfate bonds present in glycosaminoglycan (GAG) molecules such as heparan sulfate and dermatan sulfate. Hunter syndrome is a genetic disorder in which this enzyme is congenitally deleted. In the patients of Hunter syndrome, heparan sulfate and dermatan sulfate accumulate in the tissues, resulting in various symptoms such as corneal opacity, mental development delay, and so on. However, in the mild cases, mental developmental delay may not be observed. Since the fusion protein between the antibody and hI2S can degrade GAG accumulated in brain tissues by passing through BBB, it can be used as a therapeutic agent for central nervous system disorders by administered to a patient with Hunter syndrome showing mental developmental delay.

In the present invention, the term "human I2S" or "hI2S" refers to hI2S particularly having the same amino acid sequence as wild type hI2S. The wild type hI2S has an amino acid sequence consisting of 525 amino acids set forth as SEQ ID NO: 5. However, not limited to this, a hI2S containing a mutation such as substitution, deletion, addition and so on added to the amino acid sequence of the wild type hI2S is also included in hI2S, as long as it has I2S activity. When amino acids of the amino acid sequence of hI2S are substituted with other amino acids, the number of amino acids to be substituted is preferably 1 to 10, more preferably 1 to 5, still more preferably 1 to 3, and still more preferably 1 to 2. When amino acids in the amino acid sequence of hI2S are deleted, the number of amino acids to be deleted is preferably 1 to 10, more preferably 1 to 5, still more preferably 1 to 3, and still more preferably 1 to 2. A combined mutation of these addition, substitution, and deletion of amino acids can also be carried out. When adding one or more amino acids to the hI2S, they may be added inside, or on the N-terminal side or C-terminal side thereof, and the number of amino acids added is preferably 1 to 10, more preferably 1 to 5, still more preferably 1 to 3, and even more preferably 1 or 2. A combined mutation of these substitution and deletion of amino acids can also be carried out. The amino acid sequence of such a mutated hI2S has an identity of preferably not lower than 80%, more preferably not lower than 90%, still more preferably not lower than 95%, to the amino acid sequence of the original hI2S.

The statement that hI2S has the I2S activity herein means that the hI2S fused to an antibody has an activity not lower than 3% of the activity that the natural-type hI2S intrinsically has. However, the activity is preferably not lower than 10%, more preferably not lower than 20%, still more preferably not lower than 50%, even more preferably not lower than 80% of the activity that the natural-type hI2S intrinsically has. The same also applies when the I2S has one or more of mutations. The antibody is, for example, an anti-hTtR antibody.

In the present invention, the term "fusion protein" refers to a substance obtained by binding an antibody and a human lysosomal enzyme directly, or via a non-peptide linker or a peptide linker. Methods for conjugating antibodies and human lysosomal enzymes are described in detail below.

For binding an antibody to a lysosomal enzyme, a method is available to bind them together via a non-peptide linker or a peptide linker. As non-peptide linkers, there can be used polyethylene glycol, polypropylene glycol, copolymer of ethylene glycol and propylene glycol, polyoxyethylated polyol, polyvinyl alcohol, polysaccharides, dextran, polyvinyl ether, biodegradable polymer, polymerized lipid, chitins, and hyaluronic acid, or derivatives thereof, or combinations thereof. A peptide linker is a peptide chain consisting of 1 to 50 amino acids linked by peptide bonds or a derivative thereof, whose N-terminus and C-terminus are to be covalently bonded either to the antibody or the lysosomal enzyme, respectively, to bind the antibody to such a c lysosomal enzyme.

When biotin-streptavidin is used as the non-peptide linker, the antibody and a human lysosomal enzyme may be bound to each other via binding between biotin and streptavidin, where the antibody is bound to the biotin, and the human lysosomal enzyme is bound to the streptavidin. Conversely, the antibody and a human lysosomal enzyme may be bound to each other via binding between biotin and streptavidin, where the antibody is bound to the streptavidin, and the human lysosomal enzyme is bound to the biotin.

In particular, a conjugate which is formed by binding the antibody of the present invention to human lysosomal enzyme via PEG as a non-peptide linker, is designated "anti-antibody-PEG-human lysosomal enzyme". An anti-antibody-PEG-human lysosomal enzyme can be prepared by first binding the antibody to PEG to form antibody-PEG; and then binding the antibody-PEG to the human lysosomal enzyme. Alternatively, an anti-antibody-PEG-human lysosomal enzyme can be prepared by first binding the human lysosomal enzyme to PEG to form "human lysosomal enzyme-PEG", and then binding the "human lysosomal enzyme-PEG" to the antibody. In order to bind PEG to the antibody and the human lysosomal enzyme, a PEG is employed which is modified with such functional groups as carbonate, carbonylimidazole, active ester of carboxylic acid, azlactone, cyclic imide thione, isocyanate, isothiocyanate, imidate, aldehyde or the like. Such functional groups introduced to PEG react mainly with amino groups in the antibody and the human lysosomal enzyme to covalently bind PEG to the antibody and the human lysosomal enzyme. Though there is no particular limitation as to the molecular weight and the configuration of PEG employed here, its mean molecular weight (MW) is as follows: preferably MW=500 to 60000, more preferably MW=500 to 20000. For example, such PEG whose mean molecular weight is about 300, about 500, about 1000, about 2000, about 4000, about 10000, about 20000, and the like. PEG is preferably used as a non-peptide linker.

For example, "antibody-PEG" can be prepared by mixing the antibody with a polyethylene glycol having aldehyde groups as functional groups (ALD-PEG-ALD) so that the molar ratio of ALD-PEG-ALD to the antibody is 11, 12.5, 15, 110, 120 and the like, and then adding to the mixture a reducing agent such as NaCNBH$_3$ to let a reaction take place. Then, by reacting "anti-hTfR antibody-PEG" with a human lysosomal enzyme in the presence of a reducing agent such as NaCNBH$_3$, "antibody-PEG-protein" is obtained. On the contrary, it is also possible to obtain "antibody-PEG-protein" by first binding a human lysosomal enzyme to ALD-PEG-ALD to prepare "human lysosomal enzyme-PEG", and then binding the "human lysosomal enzyme-PEG" to the antibody.

The antibody and a human lysosomal enzyme can also be bound together through peptide bonds by linking the antibody heavy chain or light chain, on the C-terminal side or the N-terminal side thereof, either via a linker sequence or directly, to the N-terminus or the C-terminus of the human lysosomal enzyme, respectively. Thus the fusion protein between the antibody and a human lysosomal enzyme can be obtained by incorporating into a mammalian expression vector a DNA fragment in which a cDNA encoding the human lysosomal enzyme is placed in-frame directly, or via a DNA fragment encoding a linker sequence, on the 3'-end or 5'-end side of a cDNA encoding the heavy chain or light chain of the antibody, and culturing mammalian cells into which the above expression vector has been introduced. Where the DNA fragment encoding a human lysosomal enzyme is linked to the heavy chain, a mammalian expression vector in which a cDNA fragment encoding the antibody light chain is also introduced into the same host cells, whereas if DNA fragment encoding a human lysosomal enzyme is linked to the light chain, a mammalian expression vector in which a cDNA fragment encoding the antibody heavy chain is also incorporated into the same host cells. In the case where the antibody is a single-chain antibody, the fusion protein comprising the antibody and a human lysosomal enzyme combined can be obtained by incorporating, into an expression vector (for eukaryotic cells such as mammalian and yeast, or for prokaryotic cells such as *E. coli.*), a DNA fragment which is formed by linking the cDNA encoding a human lysosomal enzyme, on the 5'-end side or on the 3'-end side thereof, directly or via a DNA fragment encoding a linker sequence, to the cDNA encoding the single-chain antibody, and allowing the fusion protein be expressed in those cells into which the expression vector has been introduced.

In a fusion protein of the type in which a human lysosomal enzyme is linked to the antibody light chain on the C-terminal side thereof, the antibody comprises an amino acid sequence including the whole or part of the light chain variable region and an amino acid sequence including the whole or part of the heavy chain variable region, and the human lysosomal enzyme is linked to the light chain of this antibody on the C-terminal side thereof. Here, the antibody light chain and a human lysosomal enzyme may be linked together, directly or via a linker.

In a fusion protein of the type in which a human lysosomal enzyme is linked to the antibody heavy chain on the C-terminal side thereof, the antibody comprises an amino acid sequence including the whole or part of the light chain variable region and an amino acid sequence including the whole or part of the heavy chain variable region, and the human lysosomal enzyme is linked to the heavy chain of this antibody on the C-terminal side thereof. Here, the antibody heavy chain and a human lysosomal enzyme may be linked together, directly or via a linker.

In a fusion protein of the type in which a human lysosomal enzyme is linked to the antibody light chain on the N-terminal side thereof, the antibody comprises an amino acid sequence including the whole or part of the light chain variable region and an amino acid sequence including the whole or part of the heavy chain variable region, and the human lysosomal enzyme is linked to the light chain of this antibody on the N-terminal side thereof. Here, the antibody light chain and a human lysosomal enzyme may be linked together, directly or via a linker.

In a fusion protein of the type in which a human lysosomal enzyme is linked to the antibody heavy chain on the N-terminal side thereof, the antibody comprises an amino acid sequence including the whole or part of the light chain variable region and an amino acid sequence including the whole or part of the heavy chain variable region, and the human lysosomal enzyme is linked to the heavy chain of this antibody on the N-terminal side thereof. Here, the antibody heavy chain and a human lysosomal enzyme may be linked together, directly or via a linker.

In the above, when the linker sequence is placed between the antibody and a human lysosomal enzyme, the linker sequence may be a peptide chain consisting preferably of 1 to 50, more preferably of 1 to 17, still more preferably of 1 to 10, even more preferably of 1 to 5 amino acids, and in accordance with the human lysosomal enzyme to be linked to the anti-hTfR antibody, the number of amino acids of the linker sequence may be adjusted to 1, 2, 3, 1 to 17, 1 to 10, 10 to 40, 20 to 34, 23 to 31, 25 to 29, etc., as desired. Though there is no particular limitation as to amino acid sequence of the linker sequence insofar as the antibody linked by it retains the affinity to hTfR and a human lysosomal enzyme linked by the linker sequence also exhibits the protein's own physiological activity under a physiological condition, the linker may preferably be composed of glycine and serine. Examples of such linkers include one consisting of a single amino acid either glycine or serine, the amino acid sequence of Gly-Ser, the amino acid sequence of Gly-Gly-Ser, the amino acid sequence of Gly-Gly-Gly-Gly-Ser (SEQ ID NO: 1), the amino acid sequence of Gly-Gly-Gly-Gly-Gly-Ser (SEQ ID NO:2), the amino acid sequence of Ser-Gly-Gly-Gly-Gly-Gly (SEQ ID NO:3), or a sequence which includes 1 to 10 or 2 to 5 of any of those amino acid sequences consecutively linked. They have sequences consisting of 1 to 50, 2 to 17, 2 to 10, 10 to 40, 20 to 34, 23 to 31, or 25 to 29 amino acids. For example, those comprising the amino acid sequence of Gly-Ser may preferably be used as linker sequences. Same can be applied when the antibody is a single strand antibody.

Besides, in the present invention, when a peptide chain includes a plurality of linker sequences, each of those linker sequences is designated, from the N-terminal side, the first linker sequence, the second linker sequence, and so on, for convenience.

Preferred embodiments of the antibody, that antibody is a humanized antibody and an anti-human transferrin receptor antibody, include the following (x) to (z) below,
(X) the light chain comprises the amino acid sequence set forth as SEQ ID NO: 6, and the heavy chain comprises the amino acid sequence set forth as SEQ ID NO: 7;
(Y) the light chain comprises the amino acid sequence set forth as SEQ ID NO: 8, and the heavy chain comprises the amino acid sequence set forth as SEQ ID NO: 9;
(Z) the light chain comprises the amino acid sequence set forth as SEQ ID NO: 10, and the heavy chain comprises the amino acid sequence set forth as SEQ ID NO: 11. Here, (x), (y) and (z) correspond to a humanized anti-hTfR antibody No. 1, a humanized anti-hTfR antibody No. 2, and a humanized anti-hTfR antibody No. 3, respectively, that antibodies are described in the examples.

However, preferred embodiments of the antibody are not limited to the (x) to (z) above, when the antibody is a humanized antibody and an anti-human transferrin receptor antibody. For example, the antibody can be used in the present invention, whose amino acid sequence of the light chain has an identity not lower than 80% to the amino acid sequence of each one of light chain in the above (x) to (z), and whose amino acid sequence of the heavy chain has an identity not lower than 80% to the amino acid sequence of each one of heavy chain in the above (x) to (z) insofar as that antibody has affinity for hTfR. For example, the antibody can be used in the present invention, whose amino acid sequence of the light chain has an identity not lower than 90% to the amino acid sequence of each one of light chain in the above (x) to (z), and whose amino acid sequence of the heavy chain has an identity not lower than 90% to the amino acid sequence of each one of heavy chain in the above (x) to (z) insofar as that antibody has affinity for hTfR. For example, the antibody can be used in the present invention, whose amino acid sequence of the light chain has an identity not lower than 95% to the amino acid sequence of each one of light chain in the above (x) to (z), and whose amino acid sequence of the heavy chain has an identity not lower than 95% to the amino acid sequence of each one of heavy chain in the above (x) to (z) insofar as that antibody has affinity for hTfR.

Further, the antibody can be used in the present invention, which has in the light chain the amino acid sequence corresponding to the amino acid sequence introduced 1 to 10 of amino acid substitution, deletion, or addition in each one of the amino acid sequence of the light chain set forth in (x)~(z) above, and has in the heavy chain the amino acid sequence corresponding to the amino acid sequence introduced 1 to 10 of amino acid substitution, deletion, or addition in each one of the amino acid sequence of the light chain set forth in (x)~(z) above. Further, the antibody can be used in the present invention, which has in the light chain the amino acid sequence corresponding to the amino acid sequence introduced 1 to 5 of amino acid substitution, deletion, or addition in each one of the amino acid sequence of the light chain set forth in (x)~(z) above, and has in the heavy chain the amino acid sequence corresponding to the amino acid sequence introduced 1 to 5 of amino acid substitution, deletion, or addition in each one of the amino acid sequence of the light chain set forth in (x)~(z) above. Further, the antibody can be used in the present invention, which has in the light chain the amino acid sequence corresponding to the amino acid sequence introduced 1 to 3 of amino acid substitution, deletion, or addition in each one of the amino acid sequence of the light chain set forth in (x)~(z) above, and has in the heavy chain the amino acid sequence corresponding to the amino acid sequence introduced 1 to 3 of amino acid substitution, deletion, or addition in each one of the amino acid sequence of the light chain set forth in (x)~(z) above.

In the preferred embodiment (x) of the above antibody, the amino acid sequence set forth as SEQ ID NO: 15 corresponds to a variable region in the amino acid sequence of the light chain set forth as SEQ ID NO: 6, and the amino acid sequence set forth as SEQ ID NO: 16 corresponds to a variable region in the amino acid sequence of the light chain set forth as SEQ ID NO: 7. In the preferred embodiment (x) of the above antibody, the amino acid sequence set forth as SEQ ID NO: 17 corresponds to a variable region in the amino acid sequence of the light chain set forth as SEQ ID NO: 8, and the amino acid sequence set forth as SEQ ID NO: 18 corresponds to a variable region in the amino acid sequence of the light chain set forth as SEQ ID NO: 9. In the preferred embodiment (x) of the above antibody, the amino acid sequence set forth as SEQ ID NO: 19 corresponds to a variable region in the amino acid sequence of the light chain set forth as SEQ ID NO: 10, and the amino acid sequence set forth as SEQ ID NO: 20 corresponds to a variable region in the amino acid sequence of the light chain set forth as SEQ ID NO: 11. In the preferred embodiments (x) to (z) of these antibodies, the substitution, deletion or addition into the amino acid sequence constituting the amino acid sequence of the heavy chain or/and the light chain is particularly introduced into these variable regions.

In the present invention, the identity between the amino acid sequence of an unmutated antibody and the amino acid sequence of an antibody produced by introducing a mutation into it may be readily calculated using well-known homology calculator algorithms. As such algorithms, there are, for example, BLAST (Altschul SF. J Mol. Biol. 215. 403-10 (1990)), a similarity search by Pearson and Lipman (Proc. Natl. Acad. Sci. USA. 85. 2444 (1988)), and the local homology algorithm of Smith and Waterman (Adv. Appl. Math. 2. 482-9 (1981)), and the like.

Preferred embodiments of the fusion protein between the antibody and a lysosomal enzyme, that antibody is the humanized anti-hTfR antibody and that lysosomal enzyme is human iduronate-2-sulfatase (human I2S), include the following (a) to (c) below, (a) a fusion protein comprising a light chain of the humanized anti-hTfR antibody having the amino acid sequence set forth as SEQ ID NO: 6, and a heavy chain of humanized anti-hTfR antibody having the amino acid sequence set forth as SEQ ID NO: 7 and linked, on the C-terminus thereof via a linker sequence of Gly-Ser, to human iduronate-2-sulfatase set forth as SEQ ID NO: 5, (b) a fusion protein comprising a light chain of the humanized anti-hTfR antibody having the amino acid sequence set forth as SEQ ID NO: 8, and a heavy chain of humanized anti-hTfR antibody having the amino acid sequence set forth as SEQ ID NO: 9 and linked, on the C-terminus thereof via a linker sequence of Gly-Ser, to human iduronate-2-sulfatase set forth as SEQ ID NO: 5, (c) a fusion protein comprising a light chain of the humanized anti-hTfR antibody having the amino acid sequence set forth as SEQ ID NO: 10, and a heavy chain of humanized anti-hTfR antibody having the amino acid sequence set forth as SEQ ID NO: 11 and linked, on the C-terminus thereof via a linker sequence of Gly-Ser, to human iduronate-2-sulfatase set forth as SEQ ID NO: 5.

Further preferred embodiments of the fusion protein between the antibody and a lysosomal enzyme, that antibody is the humanized anti-hTfR antibody and that lysosomal enzyme is human iduronate-2-sulfatase (human I2S), include the following (a) to (c) below, (a) a fusion protein comprising a light chain of the humanized anti-hTfR antibody having the amino acid sequence set forth as SEQ ID NO: 6, and a heavy chain of the humanized anti-hTfR antibody linked, on the C-terminal side thereof and via a linker sequence of Gly-Ser, to the human iduronate-2-sulfatase, and having the amino acid sequence set forth as SEQ ID NO:12 as the whole linked heavy chain.

(b) a fusion protein comprising a light chain of the humanized anti-hTfR antibody having the amino acid sequence set forth as SEQ ID NO: 8, and a heavy chain of the humanized anti-hTfR antibody linked, on the C-terminal side thereof and via a linker sequence of Gly-Ser, to the human iduronate-2-sulfatase, and having the amino acid sequence set forth as SEQ ID NO:13 as the whole linked heavy chain, (c) a fusion protein comprising a light chain of the humanized anti-hTfR antibody having the amino acid sequence set forth as SEQ ID NO: 10, and a heavy chain of the humanized anti-hTfR antibody linked, on the C-terminal side thereof and via a linker sequence of Gly-Ser, to the human iduronate-2-sulfatase, and having the amino acid sequence set forth as SEQ ID NO:14 as the whole linked heavy chain, In the present invention, the fusion protein between the antibody and a human lysosomal enzyme may be produced by culturing a mammalian cell, which is artificially manipulated so as to produce the fusion protein by expression or strong expression of a gene encoding the fusion protein. In this end, the gene to be strongly expressed in the mammalian cells producing the fusion protein is generally introduced into the mammalian cell by transformation with an expression vector introduced with the gene. Examples of the means for artificially modifying an intrinsic gene to let it be strongly expressed include, but not limited to, replacing the promoter upstream of the intrinsic gene with a promoter which strongly induces expression of the gene. Further, though there is no particular limitation on the mammalian cells, cells derived from human, mouse, Chinese hamster are preferable, and CHO cells, the cells derived from Chinese hamster ovary cells, are particularly preferable. In the present invention, the term "fusion protein" means particularly the fusion protein secreted into the medium when mammalian cells producing the fusion protein are cultured.

A fusion protein between the antibody and a human lysosomal enzyme can also be produced by producing the antibody and a human lysosomal enzyme, respectively, and then binding these together via a non-peptide linker or a peptide linker. For this, the antibody and the human lysosomal enzyme can be produced as recombinant proteins by culturing genetically manipulated mammalian cells so as to produce these by expressing or strongly expressing the genes encoding them.

There is no particular limitation as to the expression vector for incorporating and expressing the gene encoding the fusion protein, the antibody, or a lysosomal enzyme, provided that it has the potential to let the gene express when introduced into mammalian cells. The gene incorporated in the expression vector is placed downstream of a DNA sequence (gene expression regulatory site) capable of regulating the frequency of gene transcription in mammalian cells. The gene expression regulatory site that can be used in the present invention includes, for example, cytomegalovirus-derived promoter, SV40 early promoter, human elongation factor-1 alpha (EF-1 alpha) promoter, human ubiquitin C promoter and the like.

Mammalian cells having such an introduced expression vector come to express a desired protein incorporated in the expression vector, but the expression levels vary in each of the cells. Therefore, in order to efficiently produce a recombinant protein, it is necessary to select a cell having a high expression level of the desired protein among from mammalian cells into which the expression vector has been introduced. In order to perform this selection step, the expression vector incorporates a gene that serves as a selectable marker.

The most common selection marker is an enzyme (drug resistance marker) that degrades drugs such as puromycin, neomycin, and the like. Mammalian cells will be killed in the presence of these drugs beyond certain concentrations. Mammalian cells into which an expression vector has been introduced, however, become viable in the presence of those drugs because such cells can decompose the drugs with the drug selection markers incorporated in the expression vector and thus detoxify them or weaken their toxicity. When those cells, which have been introduced with an expression vector incorporated with a drug resistance marker, are successively cultured in a selective medium containing the drug corresponding to the drug resistance marker while gradually increasing the concentration of the drug, cells that can proliferate in the presence of the drug at relatively higher concentrations are obtained. Such cells that express a drug selection marker at high levels also tend to express, at high levels, a gene encoding a protein of interest incorporated together into the expression vector, and as a result, mammalian cells thus will be obtained that express the protein of interest at high levels.

As a selection marker, glutamine synthetase (GS) may also be used. Glutamine synthetase is an enzyme synthesizing glutamine from glutamic acid and ammonia. Mammalian cells die, when cultured in a selective medium which contains an inhibitor of glutamine synthetase, such as methionine sulfoximine (MSX), but not glutamine. But when the mammalian cells have been introduced with an expression vector incorporated with glutamine synthetase, the cells become to be capable to grow in the presence of MSX at higher concentrations. At this time, if the cells are successively cultured while gradually increasing the concentration of the MSX, the result was that the cells capable of proliferating in the presence of the MSX at relatively higher concentrations are obtained. The cells selected as such a manner generally tend to express, at high levels, a gene encoding a protein of interest incorporated in the expression vector concomitantly with glutamine synthetase, and as a result, mammalian cells thus will be obtained that express the protein of interest at high levels.

As a selection marker, dihydrofolate reductase (DHFR) may also be used. When DHFR is used as the selection marker, mammalian cells are cultured in a selective medium which contains a DHFR inhibitor such as methotrexate and aminopterin. If the cells have been successively cultured while gradually increasing the concentration of the DHFR inhibitor, the cells that can proliferate in the presence of the DHFR inhibitor at relatively higher concentrations are obtained. The cells selected as such a manner generally tend to express, at high levels, a gene encoding a protein of interest incorporated in the expression vector concomitantly with DHFR, and as a result, the mammalian cells thus will be obtained that express the protein of interest at high levels.

An expression vector has been known in which glutamine synthetase (GS), as a selection marker, is located downstream of a gene encoding a protein of interest via internal ribosome entry site (IRES), (International Patent Gazette; WO02/063799, WO2013/161958). Expression vectors described in these literatures may be particularly preferable for the use in the method of production of the present invention.

For examples, an expression vector for expression of the protein can be preferably used in the method for production of the present inventions, that vector comprises a gene expression regulatory site, and a gene encoding the protein downstream thereof, an internal ribosome entry site further downstream thereof; a gene encoding a glutamine synthetase still further downstream thereof, and additionally a dihydrofolate reductase gene or a drug resistance gene downstream of either the same gene expression regulatory site or another gene expression regulatory site in addition to the former. In this expression vector, as a gene expression regulatory site or another gene expression regulatory site, a cytomegalovirus-derived promoter, an SV40 early promoter, a human elongation factor-1 alpha promoter (hEF-1 alpha promoter), and a human ubiquitin C promoter are preferable, and the hEF-1 alpha promoter is particularly preferable.

As an internal ribosome entry site, those derived from 5' untranslated regions of viruses or genes selected from the group consisting of viruses of Picornaviridae, Picornaviridae Aphthovirus, hepatitis A virus, hepatitis C virus, coronavirus, bovine enterovirus, Theiler's murine encephalomyelitis virus, Coxsackie B virus, human immunoglobulin heavy chain binding protein gene, *drosophila* antennapedia gene, and *drosophila* Ultrabithorax gene may be preferably used. The internal ribosome entry site derived from 5' untranslated regions of mouse encephalomyocarditis virus may be particularly preferably used. When an internal ribosome binding site derived from the 5' untranslated region of the mouse encephalomyocarditis virus is used, not only the wild type internal ribosome binding site, but also those of which part of the multiple start codons contained in the wild type internal ribosome binding site has been disrupted may be preferably used. Further, as a drug resistance gene to be preferably used in this expression vector, puromycin or neomycin resistance gene is preferable, and puromycin resistance gene is more preferable.

Further, for examples, an expression vector for expressing the protein can be preferably used in the method for production of the present inventions, that vector comprises hEF-1α promoter, and a gene encoding the protein downstream thereof, an internal ribosome entry site derived from 5' untranslated regions of mouse encephalomyocarditis virus further downstream thereof, a gene encoding a glutamine synthetase still further downstream thereof, and further another gene expression regulatory site and a dihydrofolate reductase gene thereof, wherein the internal ribosome binding site is that of which part of the multiple start codons contained in the wild type internal ribosome binding site has been disrupted. The expression vectors described in WO2013/161958 are the examples of such vectors.

Further, for examples, an expression vector for expressing the protein can be preferably used in the method for production of the present inventions, that vector comprises human hEF-1α promoter, and a gene encoding the protein downstream thereof, an internal ribosome entry site derived from 5' untranslated regions of mouse encephalomyocarditis virus further downstream thereof, a gene encoding a glutamine synthetase still further downstream thereof, and further another gene expression regulatory site and a drug resistance gene downstream thereof, wherein the internal ribosome binding site is that of which part of the multiple start codons contained in the wild type internal ribosome binding site has been disrupted. pE-mIRES-GS-puro described in WO2012/063799 and pE-mIRES-GS-mNeo described in WO02013/161958 are the examples of such vectors.

In the present invention, mammalian cells into which an expression vector incorporating a gene encoding the fusion protein, an antibody, or a lysosomal enzyme has been introduced are subjected to a selective culture in a selective medium to select the cells expressing the fusion protein, the antibody, or the lysosomal enzyme at high levels.

In performing a selective culture using DHFR as a selective marker, the concentration of the DHFR inhibitor in a selective medium is increased in a stepwise manner. When the DHFR inhibitor is methotrexate, the maximum concentration is preferably 0.25 to 5 µM, more preferably 0.5 to 1.5 µM, still more preferably about 1.0 µM.

When GS used as a selection marker, the concentration of the GS inhibitor in a selective medium is increased in a stepwise manner. When the GS inhibitor is MSX, the maximum concentration is preferably 100 to 1000 µM, more preferably 200 to 500 µM, and still more preferably about 300 µM. And performing this, a medium not containing glutamine is generally used as the selective medium.

When using an enzyme degrading puromycin as a selection marker, the maximum concentration of puromycin contained in a selective medium is preferably 3 to 30 µg/mL, more preferably 5 to 20 µg/mL, and still more preferably about 10 µg/mL.

When using an enzyme degrading neomycin as a selection marker, the maximum concentration of G418 contained in a selective medium is preferably 0.1 to 2 mg/mL, more preferably 0.5 to 1.5 mg/mL, and still more preferably about 1 mg/mL.

In addition, as a medium for culturing mammalian cells including the medium used for selective culture and the medium used for producing the fusion protein, an antibody, or a lysosomal protein (recombinant protein-production medium), both described later in detail, any medium can be used without particular limitation, as long as they can be used for culturing and growing mammalian cells, but a serum-free medium is preferably used.

The cells selected by the selective culture and showing a high expression level of the fusion protein, an antibody, or a lysosomal protein are used for their production as producing cells thereof. The production of the fusion protein, an antibody, or a lysosomal protein is carried out by culturing producing cells thereof in a recombinant protein-production medium. This culture is called production culture.

In the present invention, an example of serum-free media which is to be used as a recombinant protein-production medium is the medium which contains; 3 to 700 mg/mL of amino acids, 0.001 to 50 mg/L of vitamins, 0.3 to 10 g/L of monosaccharides, 0.1 to 10000 mg/L of inorganic salts, 0.001 to 0.1 mg/L of trace elements, 0.1 to 50 mg/L of nucleosides, 0.001 to 10 mg/L of fatty acids, 0.01 to 1 mg/L of biotin, 0.1 to 20 micrograms/L of hydrocortisone, 0.1 to 20 mg/L of insulin, 0.1 to 10 mg/L of vitamin $B_{12}$, 0.01 to 1 mg/L of putrescine, 10 to 500 mg/L of sodium pyruvate, and water-soluble iron compounds. As desired, it may also include thymidine, hypoxanthine, a conventional pH indicator, and antibiotics.

Further, as a serum-free medium used for the production of recombinant protein, DMEM/F12 medium, a mixed medium comprising DMEM and F12, may also be used as a basic medium. Each of these media is well known to those skilled in the art. Furthermore, as a serum-free medium, DMEM(HG)HAM modified (R5) medium may be used, too, which contains sodium hydrogen carbonate, L-glutamine, D-glucose, insulin, sodium selenite, diaminobutane, hydrocortisone, ferric (II) sulfate, asparagine, aspartic acid, serine, and polyvinyl alcohol. Furthermore, a commercially available serum-free medium may also be used as a basic medium, including CD OptiCHO™ medium, CHO—S—SFM II medium, or CD CHO medium (Thermo Fisher Scientific Inc.), EX-CELL™ 302 medium or EX-CELL™ 325-PF medium (SAFC Biosciences Inc). For example, EX-CELL™ Advanced CHO Fed-batch medium (SAFC Biosciences) which is a serum-free medium containing 0.16 μmol/L thymidine, 100 μmol/L hypoxanthine, and 4 mmol/L L-alanyl-L-glutamine may be preferably used for culturing the fusion protein-producing cells.

In the production culture of the cells producing the fusion protein, an antibody, or a lysosomal protein, the density of the producing cells thereof in the medium for recombinant protein-production is preferably adjusted to $0.2 \times 10^5$ to $5 \times 10^5$ cells/mL, more preferably $1 \times 10^5$ to $4 \times 10^5$ cells/mL, still more preferably about $2 \times 10^5$ cells/mL, when starting the culture.

Production culture has been performed while observing the cell viability (%) over time, so that the cell survival rate during the production culture is maintained preferably at 85% or more, more preferably 90% or more.

During the production culture, the culture temperature is maintained preferably at 33.5 to 37.5° C., and the dissolved oxygen saturation level during the production medium is maintained preferably at 38 to 42%, more preferably at about 40%. Here, the term "dissolved oxygen saturation level" means the dissolution amount of oxygen when the saturated dissolution amount of oxygen is taken as 100% under same conditions.

During the production culture, the production medium is stirred with an impeller (impeller). At this time, the rotational speed of the impeller is adjusted preferably to 67 to 72 rotations per minute, more preferably to 70 rotations per minute, but the rotational speed may be changed as needed depending on the shape of the impeller or the like.

Suitable culture conditions for the production culture at the early stage include, for example, such a condition in that the density of the recombinant protein-producing cells in the medium for recombinant protein production is $2 \times 10^5$ cells/mL; the culture temperature during the production culture period is maintained at 34 to 37° C.; the dissolved oxygen saturation level in the production medium is 40%; and the medium is agitated with an impeller rotating at a speed of about 89 rpm.

After completion of the production culture, the culture medium is collected. The culture supernatant is obtained by centrifuging or filtrating the collected culture. The desired fusion protein contained in the culture supernatant can be purified by a process using various chromatographies. The purification process can be carried out at room temperature or low temperature environment, but carried out preferably under a low temperature environment, and particularly preferably at a temperature of 1 to 10° C.

Hereinafter, the purification method of the fusion protein between the antibody and a human lysosomal enzyme contained in the culture supernatant is described in detail.

A step of the purification process is a column chromatography employing as solid phase a substance having affinity for the fusion protein. In this step, there is no particular limitation as to the material having an affinity for the fusion protein, but preferable are protein A, protein G, protein L, protein A/G and an antibody that recognizes the antibody constituting the fusion protein as an antigen, an antigen which is recognized by the antibody constituting the fusion protein, more preferable is protein A. The combination thereof can also be used. By loading the culture supernatant, the fusion protein contained in the culture supernatant is let bind to the column, and after washing the column, the fusion protein is eluted from the column. Thus, most of the contaminants can be removed. When the antibody constituting the fusion protein is human IgG, the antibody recognizing the antibody constituting the fusion protein as an antigen is an anti-human IgG antibody.

Among substances having an affinity for the fusion protein described above, protein A, protein G, protein L, protein A/G and an antibody that recognizes the antibody constituting the fusion protein as an antigen can be viewed as substances having an affinity for the fusion protein, but also as substances having an affinity for antibodies.

Protein A is a protein having a molecular weight of about 42 kD, present on the cell wall of Staphylococcus aureus.

Protein A can specifically bind to the Fc region of human antibodies (or humanized antibodies) of the IgG1, IgG2 and IgG4 type. Protein A can also bind to the Fab region of IgG belonging to the VH3 subfamily. Accordingly, protein A can be used when an antibody constituting a part of the fusion protein to be purified has an Fc region and is a human antibody (or humanized antibody) of IgG1, IgG2 and IgG4 type. When the antibody constituting a part of the fusion protein to be purified is Fab, F(ab'), or F(ab')$_2$ of a human antibody (or humanized antibody) belonging to the VH3 subfamily, Protein A can also be used.

Protein A used herein is not limited to wild-type protein A as long as it has the desired affinity for the antibody, but includes a mutant type protein A, wherein 1 to 10 amino acids substitution, deletion, or addition have been introduced into the amino acid sequence of the wild-type protein A Furthermore, it may be a peptide containing a partial sequence of the amino acid sequence of wild-type or mutant type protein A as long as it has the desired affinity for the antibody. Such a partial sequence includes a domain that binds to the antibody.

Protein Gs is are the proteins constituting *streptococcus* itself, and of those, "G148 protein G" having a molecular weight of about 65 kD and "C40 protein G" having a molecular weight of about 58 kD are particularly well known. Protein G can specifically bind to human antibodies (or humanized antibodies) of the IgG1, IgG2, IgG3 and IgG4 type. Accordingly, when the antibody constituting a part of the fusion protein to be purified is of the IgG3 type which does not bind to Protein A, the fusion protein can be purified by using Protein G.

The protein G used here is not limited to the wild type protein G, but a mutant type protein G containing 1 to 10 of amino acid substitution, deletion, or addition in the amino acid sequence may also be used as long as it has the desired affinity for the antibody. Furthermore, a peptide containing a partial sequence of the amino acid sequence of wild-type or a mutant type protein A may also be used as long as it has the desired affinity for the antibody. Such a partial sequence contains an antibody-binding region. The wild-type protein G has an albumin binding region, and a mutant type protein G in which such a region is deleted can be particularly suitably used in the present invention.

Protein L is one of a protein constituting the bacterial body of *Peptostreptococcus magnus*. Protein L can bind specifically to the κ chain of a light chain of a human antibody (or a humanized antibody) belonging toκI, κIII and κIV subtypes. Therefore, when an antibody constituting a part of the fusion protein to be purified has a light chain belonging to these subtypes, the protein L can be used even if the antibody is Fab or ScFv.

The protein L used here is not limited to the wild-type protein L, but a mutant type protein L containing 1 to 10 of amino acid substitution, deletion, or addition in the amino acid sequence may also be used as long as it has the desired affinity for the antibody. Furthermore, a peptide containing a partial sequence of the amino acid sequence of wild-type or a mutant type protein A may also be used as long as it has the desired affinity for the antibody. Such a partial sequence contains an antibody-binding region. The wild-type protein L has an albumin binding region, and a mutant type protein L in which such a region is deleted can be particularly suitably used in the present invention.

Protein A/G is an artificial protein produced by combining four Fc binding regions of protein A and two Fc binding regions of protein G Protein A/G has both properties of Protein G and Protein A, and it is possible to purify not only an antibody that can be purified by Protein A and but also an antibody that can be purified by Protein G.

When the antibody constituting a part of the fusion protein is human IgG the antibody which recognizes an antibody constituting a part of a fusion protein as an antigen is an anti-human IgG antibody specifically binding to this human IgG Such an anti-human IgG antibody can be prepared as a monoclonal antibody or as a polyclonal antibody by immunizing an animal with an antibody constituting a fusion protein or a part thereof as an antigen.

A substance that is recognized by the antibody constituting a part of the fusion protein as an antigen is an extracellular region of TfR, insulin receptor, leptin receptor, Lipoprotein receptor, IGF receptor, OATP-F, organic anion transporter, MCT-8, and Fc receptor, when the antibody is an anti-transferrin receptor (TfR) antibody, an anti-insulin receptor antibody, an anti-leptin receptor antibody, an anti-lipoprotein receptor antibody, an anti-IgF receptor antibody, an anti-OATP-F antibody, an anti-organic anion transporter antibody, an anti-MCT-8 antibody, an anti-monocarboxylic acid transporter antibody, and an Fc receptor antibody.

Another step of the purification process is a column chromatography employing as solid phase a substance having affinity for the phosphate group. There is no particular limitation as to the solid phase having an affinity for the phosphate group used for this, but hydroxyapatite and fluoroapatite are preferable, and hydroxyapatite is particularly preferable. It is preferable that the pH of the solution containing the fusion protein and loaded on the column chromatography is adjusted to 6.8 to 7.8 before loaded.

In the step of the purification process above, the fusion protein is let bound to the solid phase equilibrated by a buffer solution having pH near neutral and containing a salt and phosphate. The buffer solution used for this is preferably MES buffer, and its pH is preferably 6.8 to 7.8. Though there is no particular limitation for the salt contained in the buffer solution, sodium chloride is preferable, and its concentration is preferably 70 to 230 mM, more preferably 160 to 220 mM. The concentration of phosphate contained in the buffer solution is preferably 0.2 to 4.0 mM, more preferably 1 to 2.5 mM.

After washing the column to which the fusion protein is bound, the fusion protein is eluted from the column with a buffer solution having pH near neutral and containing a salt, and the fraction containing the fusion protein is recovered. The buffer solution used for this is preferably a phosphate buffer solution, and its pH is preferably 6.8 to 7.8. The concentration of phosphate contained in the buffer solution is preferably 10 to 50 mM, more preferably 20 to 40 mM. Though there is no particular limitation for the salt contained in the buffer solution, sodium chloride is preferable, and its concentration is preferably 70 to 230 mM, more preferably 160 to 220 mM. The concentration of phosphate contained in the buffer solution is preferably 0.2 to 4.0 mM.

Further another step of the purification process is a size exclusion column chromatography, which is a step for removing low molecular-weight impurities such as endotoxin, as well as multimeric complexes or decomposition products of the fusion protein. Thus, substantially pure fusion protein is obtained through this.

In the purification process of the fusion protein, a step for inactivating the virus that may be brought from the culture supernatant may optionally be added. Such an additional step for virus inactivation may be conducted prior the purification, and may be interposed between any two adjacent steps of the purification process. For example, when the purification process includes a column chromatography employing as solid phase a material coupled with a substance having affinity for the fusion protein (the first step of the purification process), a column chromatography employing as solid phase a material having affinity for phosphate group (the second step of the purification process), and a size exclusion column chromatography (the third step of the purification process) in this order, the step for virus inactivation preferably be interposed between the first and the second step of the purification processes.

The virus inactivation step is conducted by adding a nonionic surfactant to a solution containing the fusion protein and stirring at 20 to 60° C. for 2 to 6 hours. Preferable examples of the nonionic surfactant used for this include polysorbate 20, 80, and tri n-butylphosphate, or a mixture thereof.

The virus inactivation step can also be carried out using a virus removal membrane. Viruses contained in the solution can be removed by passing the solution containing the fusion protein through the virus removal membrane with a pore size of 35 nm or 20 nm.

The purified product of the fusion protein obtained by using the production method of the present invention is of such purity as is sufficient for its direct use as a medical drug. The concentration of host cell-derived proteins (HCP) contained in the purified product of the fusion protein is preferably less than 300 ppm, more preferably less than 100 ppm, for example less than 60 ppm. In addition, the proportion of the multimer in the whole fusion protein contained in the purified product of the fusion protein is preferably less than 1%.

When a purified product of a fusion protein obtained by using the production method of the present invention is provided as a medical drug, it can be provided in such a form as an aqueous preparation or a lyophilized preparation, containing an appropriate excipient. In the case of preparing the aqueous preparation, it may be filled into a vial, or it may be provided as a prefilled-type preparation filled in a syringe in advance. In the case of a freeze-dried preparation, it has been dissolved with an aqueous solution before use.

When the purified product of the fusion protein is administered as a medicament to a human, it may be administered, for example, intravenously, intramuscularly, subcutaneously, intraperitoneally, intraarterially, or intralesionally, but preferably administered intravenously.

Further, as the purified product of the fusion protein can pass through the BBB when administered to a human, it can be used as a therapeutic agent for various diseases accompanying central nervous system disorder. By administering the fusion protein, the central nervous system disorder can be prevented, ameliorated, or its progression can be delayed.

Hereinafter, described in detail is a fusion protein (humanized anti-hTfR antibody-I2S), wherein the light chain of the humanized anti-hTfR antibody has the amino acid sequence set forth as SEQ ID NO:10, and wherein the heavy chain of the humanized anti-hTfR antibody is linked, on the C-terminal side thereof and via a linker sequence set forth as Gly-Ser, to the human iduronate-2-sulfatase, and the whole linked heavy chain has the amino acid sequence set forth as SEQ ID NO:14. The antibody constituting a part of this fusion protein is of the IgG1 type.

The first step of the purification process is column chromatography employing as a solid phase a material letting a substance having an affinity for the fusion protein bound thereto. Substances having an affinity for the antibody used for this are not particularly limited, but preferred are protein A, protein G, protein L, protein A/G, anti-human IgG1 antibody, hTfR which is an antigen of the antibody, or anti-human I2S antibody, more preferably Protein A. In the case where the substance is hTfR, it is an extracellular region thereof.

When Protein A is employed as a substance having an affinity for the fusion protein in the first step, the culture supernatant containing the fusion protein is bound to a column equilibrated in advance with a buffer containing a neutral solution containing a salt. The buffer solution used for this is preferably a trometamol buffer, and its pH is preferably 6.5 to 7.5, more preferably about 7.0. Although there is no particular limitation as to the salt contained in the buffer, sodium chloride is preferable, and its concentration is preferably 60 to 180 mM, more preferably 100 to 150 mM, and still more preferably about 140 mM.

After washing the column to which the fusion protein is bound, the fusion protein is eluted with an acidic buffer containing salt, and the fraction containing the fusion protein is collected. The buffer solution used for this is preferably a glycine buffer, and its pH is preferably 3.2 to 3.8, more preferably 3.5. Although there is no particular limitation as to the salt contained in the buffer, sodium chloride is preferable, and its concentration is preferably 60 to 180 mM, more preferably 100 to 150 mM, and still more preferably about 140 mM. The pH of the solution containing the recovered fusion protein is rapidly adjusted so as to become around neutral.

The second step of the purification process is column chromatography using a material having affinity for the phosphate group as the solid phase. There is no particular limitation as to the solid phase having an affinity for the phosphoric acid group employed for this, but hydroxyapatite and fluoroapatite are preferable, and hydroxyapatite is particularly preferable.

In the second step of the purification process, when hydroxyapatite is employed as the solid phase having affinity for the phosphate group, the fusion protein is let bound to the solid phase equilibrated with a buffer at or near neutral pH containing salt and phosphoric acid. The buffer solution used for this is preferably an MES buffer, the pH of which is preferably 6.8 to 7.8, more preferably 7.3. Although there is no particular limitation as to the salt contained in the buffer, sodium chloride is preferred, and its concentration is preferably 150 to 230 mM, more preferably 215 mM. The concentration of phosphoric acid contained in the buffer is preferably 1.0 to 4.0 mM, more preferably 2.0 mM.

After washing the column to which the fusion protein is bound, the fusion protein is eluted from the column with a buffer at or near neutral pH containing a salt, and the fraction containing the fusion protein is collected. The buffer solution used for this is preferably a phosphate buffer, the pH of which is preferably 6.8 to 7.8, more preferably pH 7.3. The concentration of phosphoric acid contained in the buffer is preferably 30 to 50 mM, more preferably about 35 mM. Although there is no particular limitation as to the salt contained in the buffer, sodium chloride is preferred, and its concentration is preferably 150 to 230 mM, more preferably 215 mM.

The third step of the purification process is size exclusion column chromatography. This step is for removing low-molecular impurities such as endotoxin, multimers and degradation products of the fusion protein and the like, whereby a substantially pure fusion protein can be obtained.

In the purification process of the humanized anti-hTfR antibody-I2S, a step for inactivating the virus possibly brought from the culture supernatant may be added. This virus inactivation step may be carried out before the first step of the purification process, between any of each step in the purification process, or after completion of the purification process, For example it can be carried out prior to the first step of the purification processor between the first step and the second step of the purification process.

The virus inactivation step is carried out by adding a nonionic surfactant to a solution containing humanized anti-hTfR antibody-I2S and stirring at 20 to 60° C. for 2 to 6 hours. Preferable examples of the nonionic surfactant used for this include polysorbate 20, 80, and tri n-butylphosphate, or a mixture thereof.

The virus inactivation step may also be carried out using a virus removal membrane. By passing a solution containing humanized anti-hTfR antibody-I2S through a virus removal membrane with a pore size of 35 nm or 20 nm, the virus contained in the solution can be removed.

A purified product of the humanized anti-hTfR antibody-I2S obtained by using the method for production of the present invention is of purity that can be used as it is as a medicine. The concentration of the host cell-derived protein (HCP) contained in the purified product of the humanized anti-hTfR antibody-I2S is less than 100 ppm, for example less than 60 ppm, less than 40 ppm, or the like. Also, the proportion of the polymer in the whole humanized anti-hTfR antibody-I2S contained in the purified product of the humanized anti-hTfR antibody-I2S is less than 1%, for example less than 0.8%, less than 0.6%, less than 0.5%, and so on.

When a purified product of the humanized anti-hTfR antibody-I2S obtained by using the method for production of the present invention is supplied as a medicine, it can be supplied as an aqueous liquid preparation or a freeze-dried preparation containing an appropriate excipient. In the case of preparing an aqueous liquid preparation, it may be filled into a vial, or it may be supplied as a prefilled type preparation filled in advance in a syringe. In the case of a freeze-dried preparation, it is used by being dissolved in an aqueous medium before use.

When the purified humanized anti-hTfR antibody-I2S is administered as a pharmaceutical to humans, it can be administered, for example, intravenously, intramuscularly, subcutaneously, intraperitoneally, intraarterially, or intralesionally. For example, the purified product can be intravenously administered by drip infusion.

Further, the purified product of humanized anti-hTfR antibody-I2S can be used as a therapeutic agent for Hunter's syndrome, particularly Hunter's syndrome accompanied by central nervous disorder. The humanized anti-hTfR antibody-I2S administered to patients with Hunter's syndrome degrades glycosaminoglycans (GAG) accumulated in organs of patients, and furthermore degrade GAG accumulated in the brain tissues by passing through BBB. Therefor it can prevent, ameliorate, or delay the progress of central nervous disorders accompanying Hunter's syndrome.

EXAMPLES

While the present invention will be described in further detail below referring to examples, it is not intended that the present invention be limited to the examples.

[Example 1] Construction of Expression Vector for hI2S-Humanized Anti-hTfR Antibody Fusion Protein An expression vector for hI2S-humanized anti-hTfR antibody fusion protein was constructed using genes encoding three types of humanized anti-hTfR antibodies (Nos. 1 to 3). The antibody No. 1 comprises a light chain having the amino acid sequence set forth as SEQ ID NO:6 and a heavy chain having the amino acid sequence set forth as SEQ ID NO:7, the antibody No. 2 comprises a light chain having the amino acid sequence set forth as SEQ ID NO: 8 and a heavy chain having the amino acid sequence set forth as SEQ ID NO: 9, the antibody No. 3 comprises a light chain having the amino acid sequence set forth as SEQ ID NO: 10 and a heavy chain having the amino acid sequence set forth as SEQ ID NO: 11, respectively.

A pEF/myc/nuc vector (Invitrogen Inc.) was digested with KpnI and NcoI to cut out the region containing the EF-1α promoter and its first intron, and the region was blunt-ended with T4 DNA polymerase. A pCI-neo vector (Invitrogen) was digested with BglII and EcoRI to cut out the region containing the enhancer/promoter and intron of CMV, and then the region was blunt-ended with T4 DNA polymerase. The above region containing the EF-1α promoter and its first intron was inserted into this to construct a pE-neo vector. The pE-neo vector was digested with SfiI and BstXI and a region of approximately 1 kbp containing the neomycin resistance gene was cut out. Amplification of hygromycin gene was carried out by PCR reaction using primers Hyg-Sfi5' (SEQ ID NO:27) and Hyg-BstX3' (SEQ ID NO:28) and using pcDNA 3.1/Hygro(+) vector (Invitrogen Inc.) as a template. The amplified hygromycin gene was digested with SfiI and BstXI and inserted into the pE-neo vector from which the above neomycin resistance gene has been cut out to construct a pE-hygr vector. A method for constructing the pE-hygr vector is also disclosed in Patent Document (JP2009-273427A).

A DNA fragment set forth as SEQ ID NO:21 and containing the gene encoding the full length of the light chain of the humanized anti-hTfR antibody No. 1 having the amino acid sequence set forth as SEQ ID NO:6 was artificially synthesized. A MluI sequence was introduced on the 5' side of this DNA fragment and a NotI sequence on the 3' side thereof. This DNA fragment was digested with MluI and NotI and incorporated between MluI and NotI of the pE-neo vector. The obtained vector was designated pE-hygr (LC1) which is a vector for expressing the light chain of humanized anti-hTfR antibody No. 1.

A DNA fragment (SEQ ID NO: 22) containing a gene encoding the full length of the light chain of humanized anti-hTtR antibody No. 2 having the amino acid sequence set forth as SEQ ID NO:8 was artificially synthesized. The MluI sequence was introduced on the 5' side of this DNA fragment and the Not sequence on the 3' side thereof. This DNA fragment was digested with MluI and NotI and incorporated between MluI and NotI of the pE-neo vector. The resulting vector was designated pE-hygr(LC 2) which is a vector for expressing the light chain of humanized anti-hTfR antibody No. 2.

A DNA fragment (SEQ ID NO: 23) containing a gene encoding the full length of the light chain of humanized anti-hTfR antibody No. 3 having the amino acid sequence set forth as SEQ ID NO: 10 was artificially synthesized. The MluI sequence was introduced on the 5' side of this DNA fragment and the NotI sequence on the 3' side thereof.

This DNA fragment was digested with MluI and Not and incorporated between MluI and NotI of the pE-neo vector. The obtained vector was defined as pE-hygr(LC3) which is a vector for expressing the light chain of humanized anti-hTfR antibody No. 3.

A DNA fragment was artificially synthesized, having a nucleotide sequence set forth as SEQ ID NO:24 containing a gene encoding a protein in which hI2S having an amino acid sequence set forth as SEQ ID NO:5 is linked to the C-terminal side of the heavy chain of the humanized anti-hTfR antibody No. 1 having an amino acid sequence set forth as SEQ ID NO:7 via a linker having an amino acid sequence set forth as (Gly-Ser). This DNA fragment encodes a protein having the amino acid sequence set forth as SEQ ID NO:12, in which a heavy chain of humanized anti-hTfR antibody No. 1 binds to hI2S. This DNA fragment was digested with MluI and Not and inserted between MluI and NotI of the pE-neo vector to construct pE-neo (HC-I2S-1).

A DNA fragment having a nucleotide sequence set forth as SEQ ID NO:25 containing a gene encoding a protein in which hI2S having an amino acid sequence set forth as SEQ ID NO:5 is linked to the C-terminal side of the heavy chain of the humanized anti-hTfR antibody No. 2 having an amino acid sequence set forth as SEQ ID NO:9 via a linker having an amino acid sequence set forth as (Gly-Ser) was artificially synthesized. This DNA fragment encodes a protein having the amino acid sequence set forth as SEQ ID NO:13, in which a heavy chain of humanized anti-hTfR antibody No. 2 binds to hI2S. This DNA fragment was digested with MluI and NotI and integrated between MluI and NotI of the pE-neo vector to construct pE-neo (HC-I2S-2).

A DNA fragment having a nucleotide sequence set forth as SEQ ID NO:26 containing a gene encoding a protein in which hI2S having an amino acid sequence set forth as SEQ ID NO:5 is linked to the C-terminal side of the heavy chain of the humanized anti-hTfR antibody No. 3 having an amino acid sequence set forth as SEQ ID NO:11 via a linker having an amino acid sequence set forth as (Gly-Ser) was artificially synthesized. This DNA fragment encodes a protein having the amino acid sequence shown in SEQ ID NO:14, in which a heavy chain of humanized anti-hTfR antibody No. 3 binds to hI2S. This DNA fragment was digested with MluI and NotI and integrated between MluI and NotI of the pE-neo vector to construct pE-neo (HC-I2S-3).

[Example 2-1] Preparation of a High Expression Cell Lines of hI2S-Humanized Anti-hTfR Antibody Fusion Proteins CHO cells (CHO-K1 obtained from American Type Culture Collection) were transformed with combinations of pE-hygr (LC1) and pE-neo (HC-I2S-1) constructed in Example 1, pE-hygr (LC2) and pE-neo (HC-I2S-2) constructed in Example 1 and pE-hygr (LC3) and pE-neo (HC-I2S-3) constructed in Example 1, respectively, using the GenePulser (Bio-Rad Inc.).

Transformation of cells was in brief carried out by the following method. $5 \times 10^5$ CHO-K1 cells were seeded in a 3.5 cm culture dish to which CD OptiCHO™ medium (Thermo Fisher Scientific Inc.) was added and cultured overnight at 37° C. under 5% $CO_2$. After the culture, the cells were suspended in Opti-MEM™I medium (Thermo Fisher Scientific Inc.) to a density of $5 \times 10^6$ cells/mL. 100 μL of the cell suspension was collected, and thereto 5 μL each of the pE-hygr (LC1) and pE-neo (HC-I2S-1) plasmid DNA solutions both having been diluted to 100 μg/mL with CD OptiCHO™ medium was added. Electroporation was performed using GenePulser (Bio-Rad Inc.), and plasmids were introduced into the cells. After overnight culture under the condition of 37° C., 5% $CO_2$, the cells were selectively cultured in CD OptiCHO™ medium supplemented with 0.5 mg/mL of hygromycin and 0.8 mg/mL of G418. For the combination of pE-hygr (LC2) and pE-neo (HC-I2S-2) and the combination of pE-hygr (LC3) and pE-neo (HC-I2S-3), the transformations of the cells were conducted by the same method.

Then, the cells selected above through the selection culture were seeded on 96-well plates so that not more than one cell might be seeded per well by limiting dilution. The cells then were cultured for about 10 days so that monoclonal colonies were formed. Respective culture supernatants of the wells in which monoclonal colony was formed were collected, the amount of the humanized antibody contained in culture supernatants was determined by ELISA, and the hI2S-humanized anti-hTfR antibody fusion protein high-expressing cell lines were selected.

The ELISA above was conducted as follows in general. To each well of 96-well microtiter plates (Nunc Inc.) were added 100 μL, of a goat anti-human IgG polyclonal antibody solution diluted with 0.05 M sodium bicarbonate buffer (pH 9.6) to 4 μg/mL, and the plate was left to stand for at least one hour at room temperature so as to allow the antibody to be adsorbed with the plates. Then, after each well was washed three times with a phosphate-buffered saline (pH 7.4) supplemented with 0.05% Tween 20 (PBS-T), 200 μL, of Starting Block (PBS) Blocking Buffer (Thermo Fisher Scientific Inc.) was added to each well, and the plates were left to stand for 30 minutes at room temperature. After each well was washed with PBS-T three times, the culture supernatant or the human IgG reference standard product which had been diluted with a phosphate buffer saline (pH 7.4) supplemented with 0.5% BSA and 0.05% Tween 20 (PBS-BT) to appropriate concentrations, was added to each well, in the amount of 100 μL, and the plates were left to stand for at least one hour at room temperature. After the plates were washed three times with PBS-T, 100 μL of HRP-labeled anti-human IgG polyclonal antibody solution which had been diluted with PBS-BT, was added to each well, and the plates were left to stand for at least one hour at room temperature. After the wells were washed three times with PBS-T, 0.4 mg/mL o-phenylenediamine in citrate-phosphate buffer (pH 5.0) was added to each well, in the amount of 100 μL, and the wells were left to stand for 8 to 20 minutes at room temperature. Then, 1 mol/L sulfuric acid was added to each well, in the amount of 100 μL to terminate the reaction, and the absorbance for each well was measured at 490 nm using a 96-well plate reader. The cells corresponding to the wells which exhibited the higher measurements were regarded as a high-expressing cell line for hI2S-humanized anti-hTfR antibody fusion protein.

A high-expressing cell line of a hI2S-humanized anti-hTfR antibody fusion protein obtained by transformation with combination of pE-hygr(LC1) and pE-neo(HC-I2S-1) was designated as a hI2S-anti-hTfR antibody expressing strain 1. The fusion protein of hI2S and humanized anti-hTfR antibody expressed by this cell line was designated as I2S-anti-hTfR antibody 1.

A high-expressing cell line of a hI2S-humanized anti-hTfR antibody fusion protein obtained by transformation with combination of pE-hygr(LC2) and pE-neo(HC-I2S-2) was designated as a hI2S-anti-hTfR antibody expressing strain 2. The fusion protein of hI2S and humanized anti-hTfR antibody expressed by this cell line was designated as I2S-anti-hTfR antibody 2.

A high-expressing cell line of a hI2S-humanized anti-hTfR antibody fusion protein obtained by transformation with combination of pE-hygr(LC3) and pE-neo(HC-I2S-3) was designated as a hI2S-anti-hTfR antibody expressing strain 3. The fusion protein of hI2S and humanized anti-hTfR antibody expressed by this cell line was designated as I2S-anti-hTfR antibody 3.

[Example 3] Preparation of High Expression Cell Line of hI2S-Humanized Anti-hTfR Antibody Fusion Protein The hI2S-anti-hTfR antibody expressing strains 1 to 3 obtained in Example 2 were suspended in CD OptiCHO™ medium containing 10 mg/L insulin, 40 mg/mL thymidine, and 10% (v/v) DMSO, and dispensed into cryotubes and stored as seed cells in liquid nitrogen.

[Example 4] Culture of hI2S-Anti-hTfR Antibody Expressing Strain

The hI2S-anti-hTfR antibodies were produced by the method described below. The hI2S-anti-hTfR antibody expressing strain 3 obtained in Example 2-1 was suspended in about 200 L of serum-free medium (EX-CELL Advanced CHO Fed-batch Medium, Sigma Aldrich Inc.) containing 4 mM L-alanyl-L-glutamine, 100 μmol/L hypoxanthine and 16 μmol/L thymidine to the density of about $2 \times 10^5$ cells/mL. 140 L of this cell suspension was transferred to a culture tank. The medium was stirred with an impeller at a rate of 89 rpm, the dissolved oxygen saturation of the medium was kept at about 40%, and the cells were cultured for about 11 days at a temperature range of 34 to 37° C. During the culture period, cell number, cell viability, medium glucose concentration, and lactate concentration were monitored. When the glucose concentration of the medium became less than 15 mmol/L, the glucose solution was added to the medium immediately so that the glucose concentration became 37.89 mmol/L. After completion of the culture, the medium was collected. The recovered medium was filtered with Millistak+HC Pod Filter grade D0HC (Merck Inc.) and further filtered with Millistak+HCgrade X0HC (Merck Inc.) to obtain a culture supernatant containing I2S-anti-hTfR antibody 3. The culture supernatant was subjected to ultrafiltration using a Pellicon™ 3 Cassette w/Ultracel PLCTK Membrane (pore size: 30 kDa, membrane area: 1.14 m², Merck Inc.) and concentrated until the liquid volume was about 1/17. The concentrate was then filtered using OpticapXL600 (0.22 µm, Merck Inc.). The obtained solution was used as a concentrated culture supernatant.

[Example 5] Virus Inactivation

To the concentrated culture supernatant obtained in Example 4, tri-n-butyl phosphate (TNBP) and polysorbate 80 were added so that the final concentrations were 0.3% (v/v) and 1% (w/v), respectively, and gently stirred at room temperature for 4 hours. This procedure is conducted for inactivating the virus contaminating the culture supernatant. However, as long as culturing is carried out using a serum-free medium not containing biological components, there is little possibility that viruses harmful to the human body are contaminated in the culture supernatant.

[Example 6] Purification of hI2S-Anti-hTfR Antibody

The concentrated culture supernatant after the virus inactivation was added to a Millipak-200 Filter Unit (pore size: 0.22 µm, Merck Inc.) after adding thereto 20 mM Tris-HCl buffer (pH 7.0) containing 0.5 volume of 140 mM NaCl. The solution after filtration was loaded onto a MabSelect SuRe LX column (column volume: about 3.2 L, bed height: about 20 cm, GE Healthcare Inc.), which was a protein A affinity column, equilibrated with 4 column volumes of 20 mM Tris-HCl buffer (pH 7.0) containing 140 mM NaCl, at a constant flow rate of 200 cm/hr to adsorb I2S-anti-hTfR antibody 3 to protein A.

Subsequently, the column was washed with 5 column volumes of 10 mM Tris-HCl buffer (pH 7.0) containing 500 mM NaCl and 450 mM arginine at the same flow rate. Then the column was further washed with 2.5 column volumes of 20 mM Tris-HCl buffer (pH 7.0) containing 140 mM NaCl at the same flow rate. Then I2S-anti-hTfR antibody 3 adsorbed to Protein A was eluted with 5 column volumes of 100 mM glycine buffer (pH 3.5) containing 140 mM NaCl. The eluate was immediately neutralized by receiving in a container containing 1 M Tris-HCl buffer (pH 7.5) in advance.

To the above eluate from the Protein A affinity column, 200 mM phosphate buffer (pH 7.0), 10 mM MES buffer (pH 7.3) containing 4 M NaCl and 2 mM phosphate buffer, and 1 M Tris-HCl buffer solution (pH 8.0) were added in the order, and the concentrations of sodium phosphate and NaCl contained in the eluate were adjusted to 2 mM and 215 mM, respectively, and the pH of the eluate was adjusted to 7.3. The eluate was then filtered through Opticap XL 600 (pore size: 0.22 µm, Merck Inc.). The solution after filtration was applied to a CHT Type II 40 µm column, a hydroxyapatite column (Column volume: about 3.2 L, bed height: about 20 cm, Bio-Rad Inc.), equilibrated with 4 column volumes of 10 mM MES buffer solution (pH 7.3) containing 215 mM NaCl and 2 mM sodium phosphate at a constant flow rate of 200 cm/hr to adsorb I2S-anti-hTfR antibody 3 to hydroxyapatite.

Subsequently, the column was washed with 5 column volumes of the same buffer at the same flow rate. Then I2S-anti-hTfR antibody 3 adsorbed on hydroxyapatite was eluted with 5 column volumes of 35 mM phosphate buffer (pH 7.3) containing 215 mM NaCl. Purification by the hydroxyapatite column was carried out in two portions using half volume of the eluate from the protein A affinity column.

To the above eluate from the hydroxyapatite column, dilute hydrochloric acid was added to adjust the pH to 6.5. Then, ultrafiltration was carried out using Pellicon™ 3 Cassette w/Ultracel PLCTK Membrane (pore size: 30 kDa, membrane area: 1.14 m 2, Merck Inc.) to concentrate I2S-antihTfR antibody 3 in the solution at the concentration of about 2 mg/mL. The concentrate was then filtered using Opticap XL 600 (0.22 µm, Merck Inc.).

The above concentrated solution was applied to a Superdex 200 column, size exclusion column (Column volume: about 12.6 L, bed height: 40 cm, GE Healthcare Inc.) equilibrated with 5 column volumes of 20 mM phosphate buffer (pH 6.5) containing 0.8 mg/mL NaCl and 75 mg/mL sucrose at a constant flow rate of 19 cm/hr, and the same buffer was supplied at the same flow rate. At this time, an absorbance photometer for continuously measuring the absorbance of the eluate was placed in the flow path of the eluate from the size exclusion column, and the absorbance at 280 nm was monitored, the fractions which corresponded to an absorption peak at 280 nm were collected as a fractions containing I2S-anti-hTfR antibody 3, which was used as a purified product of I2S-anti-hTfR antibody. Purification on the size exclusion column was carried out in two portions using half volume of the eluate from the hydroxyapatite column.

[Example 7] Measurement of Recovery Rate of I2S-Anti-hTfR Antibody in Each Purification Step The amount of I2S-anti-hTfR antibody 3 loaded and recovered in the eluate in each purification step were measured using the ELISA method described in Example 2. The results are shown in Table 1.30.6 g of I2S-anti-hTfR antibody 3, corresponding to approximately 76.5% of 36.7 g of I2S-anti-hTfR antibody 3 contained initially in the culture supernatant, was recovered as a purified product. These results indicate that the purification method described in the above examples is very efficient as a purification method of I2S-anti-hTfR antibody 3. In Table 1, the process recovery rate (%) means the ratio of the recovered rhI2S amount to the loaded amount of rhI2S in each purification process, and the total recovery rate (%) means the ratio of the amount of rhI2S recovered in each purification step to the initial amount of rhI2S used in the purification step.

TABLE 1

Recovery rate of I2S-anti-hTfR antibody 3 in each purification step

| Purification Step | I2S-anti-hTfR antibody 3 | | | |
|---|---|---|---|---|
| | loaded amount (g) | Eluted amount (g) | process recovery rate (%) | total recovery rate (%) |
| Protein A affinity column | 36.7 | 34.6 | 100.1 | 100.1 |
| Hydroxyapatite column | 34.1 | 31.4 | 92.1 | 90.9 |
| Gel filtration column | 30.6 | 26.5 | 86.4 | 76.5 |

[Example 8] Analysis of Purified Product of I2S-Anti-hTfR Antibody (Quantification of HCP)

The amount of host cell-derived protein (HCP) contained in the purified product of I2S-anti-hTfR antibody was quantified by ELISA method. At first, 100 µL of anti-CHO cell-derived protein antibody was added to each well of a 96-well plate (Nunc Inc.), and let stand overnight to adsorb the antibody. After washing each well three times, 200 µL of a blocking solution containing casein was added to each well and the plate was shaken at 25° C. for 60 minutes. After washing each well three times, 100 µL each of a solution (sample solution) containing a purified product of I2S-anti-hTfR antibody or HCP standard solution was added to each well, followed by shaking at 25° C. for 2 hours. After washing each well three times, 100 µL of biotinylated anti-CHO cell-derived protein antibody was added to each well and the plate was shaken at 25° C. for 60 minutes. After washing each well three times, 100 µL of HRP-conjugated streptavidin (Jackson Immuno Research Laboratories Inc.) was added and the plate was shaken at 25° C. for 60 minutes. After washing each well three times, 100 µL of TMB substrate solution was added to each well and the plate was shaken at 25° C. to develop color. As the TMB substrate solution, a mixture of TMB peroxidase substrate and peroxidase substrate solution B, both included in TMB microwell peroxidase substrate system (KPL Inc.), in equal amount was used. After color development, 100 µL of 1 mol/L sulfuric acid was added to each well to stop the enzymatic reaction, and the absorbance at 450 nm in each well was measured using a 96-well plate reader. A standard curve was produced on the measurement value of the HCP standard solution, and the value of the sample solution was interpolated to the standard curve to quantify the HCP contained in the purified product of the I2S-anti-hTfR antibody. The HCP contained in the purified product of the I2S-anti-hTfR antibody was quantified from the quantified value of HCP thus determined and the quantitative value of the purified product of I2S-anti-hTfR antibody measured by the ELISA method described in Example 2. As a result, it was found that the amount of HCP contained in the purified product of I2S-anti-hTfR antibody was about 35 ppm (ie, about 35 ng of HCP per 1 mg of I2S-anti-hTfR antibody purified product).

[Example 9] Analysis of Purified Product of I2S-Anti-hTfR Antibody (SE-HPLC Analysis)

TSK gel UltraSW Aggregate column (inner diameter 7.8 mm×height 30 cm, Tosoh Corporation Inc.) was set in UV/VIS detector of SPD-20 AV, the LC-20A system (Shimadzu Corporation). The column was equilibrated with 200 mM phosphate buffer (pH 6.5) containing 5% propanol and 20 mM NaCl. To this column, 10 µL of a solution containing the purified product of I2S-anti-hTfR antibody obtained in Example 6 at a concentration of 1 mg/mL was loaded at a constant flow rate of 0.5 mL/min, and the same buffer was supplied at the same flow rate. FIG. 1 shows the elution profile obtained by measuring the absorbance at 215 nm. The obtained profile showed almost only a single peak corresponding to I2S-anti-hTfR antibody 3. However, a peak (peak B in the figure) derived from the polymer of I2S-anti-hTfR antibody 3 detected prior to the main peak (peak A in the figure) was observed. From the ratio of the area of the peak B to the area of the whole peak, the ratio of the polymer to the whole I2S-anti-hTfR antibody 3 was calculated to be about 0.49%.

[Example 10] Analysis of Purified Product of I2S-Anti-hTfR Antibody (Summary)

The results of analysis of the purified product of the I2S-anti-hTfR antibody described above indicate that the purified product of the I2S-anti-hTfR antibody obtained in Example 6 contains almost no impurities including HCP and that the abundance ratio of the polymer is extremely low. That is, it is concluded that the purified product of I2S-anti-hTfR antibody has the quality to permit its use as a medicine as it is, for example, as an intravenously, intramuscularly, subcutaneously, intraperitonealy, intraarterialy or intralesionaly administered medicine.

[Example 11] Culture of hI2S-Anti-hTfR Antibody Expressing Strain (Alternative Method)

The seed cells of the hI2S-anti-hTfR antibody expressing strain 3 obtained in Example 3 were thawed in a 37° C. water bath. The cells were cultured with shaking in serum-free medium (EX-CELL Advanced CHO Fed-batch Medium, Sigma Aldrich Inc.) containing 4 mM L-alanyl-L-glutamine, 100 µmol/L hypoxanthine, 16 µmol/L thymidine, 500 µg/mL hygromycin B, and 10 µg/mL puromycin at a density of $4 \times 10^5$ cells/mL for 3 days under the conditions of 37° C. and 5% $CO_2$. This culture was repeated until the cell number grew to at least $5 \times 10^{11}$ cells.

Subsequently, the cells were suspended in serum-free medium (EX-CELL Advanced CHO Fed-batch Medium, Sigma Aldrich Inc.) supplemented with 4 µmM L-alanyl-L-glutamine, 100 µmol/L hypoxanthine, and 16 µmol/L thymidine so that the cell density became about $2 \times 10^5$ cells/mL. About 1400 L of this cell suspension was transferred to a culture tank and stirred with an impeller at a rate of 80 rpm, and the pH of the medium was kept at 6.9 and the dissolved oxygen saturation at about 40%, and cells were cultured for about 11 days while adjusting the culture temperature at the range of 34~37° C. Further, 70 L of EX-CELL Advanced CHO Feed 1 containing 35 g/L glucose was added daily from day 3 to day 10. Sampling was carried out every day during culturing, and cell number, viability, glucose concentration, lactic acid concentration were measured. The expression level of anti-hTfRAb-I2S was measured from day 5 to day 11. When the glucose concentration became less than 15 mmol/L, glucose was immediately added so as to have its concentration to be 37.89 mmol/L.

After completion of the culture, the medium was collected. The collected medium was filtered through Millistak+HC Pod Filter grade D0HC (Merck Inc.) and further filtered through Millistak+HCgrade X0HC (Merck Inc.) to obtain a culture supernatant containing I2S-anti-hTfR antibody 3. The culture supernatant was subjected to ultrafiltration using a Pellicon™ 3 Cassette w/Ultracel PLCTK Membrane (pore size: 30 kDa, membrane area: 9.12 m², Merck Inc.) and concentrated until the liquid volume was about ⅓. The concentrate was then filtered using Opticap XL 600 (0.22 μm, Merck Inc.). The obtained solution was used as a concentrated culture supernatant.

[Example 12] Purification of hI2S-Anti-hTfR Antibody (Alternative Method)

A ⅓ volume of the concentrated culture supernatant obtained in Example 11 was loaded on a MabSelect SuRe LX column (column volume: about 9.8 L, bed height: about 20 cm, GE Healthcare Inc.), a Protein A affinity column, equilibrated with 140 column volumes of 20 mM Tris-HCl buffer (pH 7.0) containing 140 mM NaCl at a constant flow rate of 200 cm/hr to adsorb I2S-anti-hTfR antibody 3 to Protein A.

Subsequently, the column was washed by supplying 5 column volumes of 10 mM Tris-HCl buffer (pH 7.0) containing 500 mM NaCl and 450 mM arginine at the same flow rate. Then the column was washed with 2.5 column volumes of 20 mM Tris-HCl buffer (pH 7.0) containing 140 mM NaCl at the same flow rate. Then I2S-anti-hTfR antibody 3 adsorbed on Protein A was eluted with 5 column volumes of 100 mM glycine buffer (pH 3.5) containing 140 mM NaCl. The eluate was immediately neutralized by collecting in a container containing 100 mM MES buffer (pH 7.0).

Polysorbate 80 was added to the above eluate from the protein A affinity column so that the final concentration was to be 1% (w/v), and the mixture was gently stirred at room temperature for 3 hours or more. This step is for inactivating viruses that may be contaminating the eluate.

To the above solution after the virus inactivation, 200 mM phosphate buffer (pH 7.0), 10 mM MES buffer (pH 7.3) containing 4 M NaCl and 2 mM phosphate buffer, and 1 M Tris-HCl buffer solution (pH 8.8) were added in the order, and the concentrations of sodium phosphate and NaCl contained in the eluate were adjusted to 2 mM and 215 mM, respectively, and the pH of the eluate was adjusted to 7.3. The eluate was then filtered through OPTICAP SHC XL 3 (0.22 μm, Merck Inc.). The solution after filtration was applied to a hydroxyapatite column, CHT Type II 40 μm column (volume of column: about 19.2 L, bed height: about 20 cm, Bio-Rad Inc.), equilibrated with 4 column volumes of 10 mM MES buffer (pH 7.3) containing 215 mM NaCl and 2 mM phosphate buffer at a constant flow rate of 200 cm/hr to a column to adsorb I2S-anti-hTfR antibody 3 on hydroxyapatite.

Subsequently, the column was washed by supplying 5 column volumes of same buffer at the same flow rate. Then I2S-anti-hTfR antibody 3 adsorbed on hydroxyapatite was eluted with 5 column volumes of 35 mM phosphate buffer (pH 7.3) containing 215 mM NaCl.

To the above eluate from the hydroxyapatite column, dilute hydrochloric acid was added to adjust the pH to 6.5. Subsequently, ultrafiltration was carried out using Pellicon™ 3 Cassette w/Ultracel PLCTK Membrane (pore size: 30 kDa, membrane area: 2.85 m², Merck Inc.) to concentrate I2S-antihTfR antibody 3 in the solution at the concentration of about 20 mg/mL. The concentrate was then filtered using Opticap XL 600 (0.22 μm, Merck Inc.).

The above concentrated solution was applied to a Superdex 200 column, size exclusion column (column volume: about 38.5 L, bed height: 40 cm, GE Healthcare Inc.) equilibrated with 5 column volumes of 20 mM phosphate buffer (pH 6.5) containing 0.8 mg/mL NaCl and 75 mg/mL sucrose at a flow rate of 24 cm/hr or less, and the same buffer was supplied at the same flow rate. At this time, an absorbance photometer for continuously measuring the absorbance of the eluate was placed in the flow path of the eluate from the size exclusion column, and the absorbance at 280 nm was monitored, the fractions which corresponded to an absorption peak at 280 nm were collected as a fraction containing I2S-anti-hTfR antibody 3. The recovered solution was filtered with Planova 20N (size: 0.3 m 2, Asahi Kasei Medical Inc.) and Millipak-100 Filter Unit (pore diameter. 0.22 μm, Merck Inc.). The solution after filtration was designated as purified product of I2S-anti-hTfR antibody.

[Example 13] Measurement of Recovery Rate of I2S-Anti-hTfR Antibody in Each Purification Step (Alternative Method)

The amount of I2S-anti-hTfR antibody 3 loaded and recovered in the eluate in each purification step (alternative method) were measured using the ELISA method described in Example 2. The results are shown in Table 2. 68.8 g of I2S-anti-hTfR antibody 3, corresponding to approximately 82% of 96.8 g of I2S-anti-hTfR antibody 3 contained initially in the culture supernatant, was recovered as a purified product. These results indicate that the purification method (alternative method) described in the above Example 12 is very efficient as a purification method of the I2S-anti-hTfR antibody. Meanings of process recovery rate (%) and total recovery rate (%) in Table 3 are the same as those used in Table 1.

TABLE 2

Recovery rate of I2S-anti-hTfR antibody 3 in each purification step

| | I2S-anti-hTfR antibody 3 | | | |
|---|---|---|---|---|
| Purification Step | loaded amount (g) | Eluted amount (g) | process recovery rate (%) | total recovery rate (%) |
| Protein A affinity column | 96.8 | 100.1 | 103.3 | 103.3 |
| Hydroxyapatite column | 93.7 | 81.1 | 86.6 | 89.5 |
| Gel filtration column | 68.8 | 62.8 | 91.3 | 81.7 |

[Example 14] Analysis of Purified Product of I2S-Anti-hTfR Antibody Obtained by Alternative Method (Quantification of HCP)

For the purified product of I2S-anti-hTfR antibody obtained in Example 12, The amount of HCP was quantified by the method described in Example 8. The results indicate that the amount of HCP contained in the purified product of I2S-anti-hTfR antibody was about 20 ppm (ie, about 20 ng of HCP per 1 mg of I2S-anti-hTfR antibody purified product).

[Example 15] Analysis of Purified Product of I2S-Anti-hTfR Antibody Obtained by Alternative Method (SE-HPLC Analysis)

Figure 2:
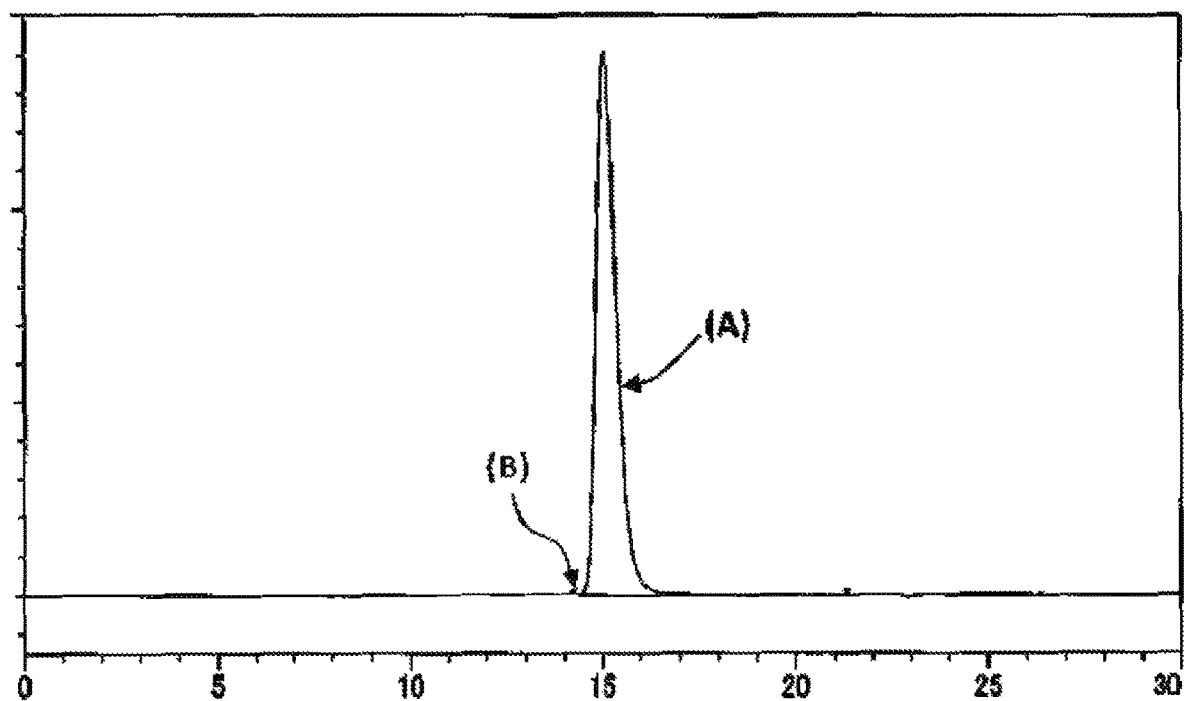
FIG. 2 shows the SE-HPLC chart of the purified product of I2S-anti-hTfR antibody obtained in Example 12. The vertical axis shows absorbance at 215 nm, and the horizontal axis shows retention time. (A): a peak corresponding to monomer of I2S-anti-hTfR antibody 3, (B): a peak corresponding to multimer of I2S-anti-hTfR antibody 3.

SE-HPLC analysis was performed for the purified product of I2S-anti-hTfR antibody obtained in Example 12 by the method described in Example 9. The analytical result is shown in FIG. 2. The obtained profile showed almost only a single peak corresponding to I2S-anti-hTfR antibody 3. However, a peak (peak B in the figure) derived from the polymer of I2S-anti-hTfR antibody 3 detected prior to the main peak (peak A in the figure) was observed. From the ratio of the area of the peak B to the area of the whole peak, the ratio of the polymer to the whole I2S-anti-hTfR antibody 3 was calculated to be about 0.37%.

[Example 16] Analysis of Purified Product of I2S-Anti-hTfR Antibody Obtained by Alternative (Summary)

The results of analysis of the purified product of the I2S-anti-hTfR antibody described above indicate that the purified product of the I2S-anti-hTfR antibody obtained in Example 12 contains almost no impurities including HCP and that the abundance ratio of the polymer is extremely low. That is, it is concluded that the purified product of I2S-anti-hTfR antibody has the quality to permit its use as a medicine as it is, for example, as an intravenously, intramuscularly, subcutaneously, intraperitonealy, intraarterialy or intralesionaly administered medicine.

INDUSTRIAL APPLICABILITY

According to the present invention, for example, a fusion protein in which an antibody is fused with another protein can be provided, that fusion protein is purified to such a purity as permits its direct use as a medicine.

Sequence Listing Free Text

SEQ ID NO:1=Amino acid sequence of an exemplified linker 1
SEQ ID NO:2=Amino acid sequence of an exemplified linker 2
SEQ ID NO:3=Amino acid sequence of an exemplified linker 3
SEQ ID NO:6=Amino acid sequence of the light-chain of humanized anti-hTfR antibody No. 1
SEQ ID NO:7=Amino acid sequence of the heavy-chain of humanized anti-hTfR antibody No. 1
SEQ ID NO:8=Amino acid sequence of the light-chain of humanized anti-hTfR antibody No. 2
SEQ ID NO:9=Amino acid sequence of the heavy-chain of humanized anti-hTfR antibody No. 2
SEQ ID NO:10=Amino acid sequence of the light-chain of humanized anti-hTfR antibody No. 3
SEQ ID NO:11=amino acid sequence of the heavy-chain of humanized anti-hTfR antibody No. 3
SEQ ID NO:12=Amino acid sequence of fusion protein of the heavy-chain of humanized anti-hTfR antibody No. 1 and hI2S
SEQ ID NO:13=Amino acid sequence of fusion protein of the heavy-chain of humanized anti-hTfR antibody No. 2 and hI2S
SEQ ID NO:14=Amino acid sequence of fusion protein of the heavy-chain of humanized anti-hTfR antibody No. 3 and hI2S
SEQ ID NO:15=Amino acid sequence of the light-chain variable region of humanized anti-hTfR antibody No. 1
SEQ ID NO:16=Amino acid sequence of the heavy-chain variable region of humanized anti-hTfR antibody No. 1
SEQ ID NO:17=Amino acid sequence of the light-chain variable region of humanized anti-hTfR antibody No. 2
SEQ ID NO:18=Amino acid sequence of the heavy-chain variable region of humanized anti-hTfR antibody No. 2
SEQ ID NO:19=Amino acid sequence of the light-chain variable region of humanized anti-hTfR antibody No. 3
SEQ ID NO:20=Amino acid sequence of the heavy-chain variable region of humanized anti-hTfR antibody No. 3
SEQ ID NO:21=Nucleotide sequence encoding amino acid sequence of the light-chain of humanized anti-hTfR antibody No. 1, synthetic sequence
SEQ ID NO:22=Nucleotide sequence encoding amino acid sequence of the light-chain of humanized anti-hTfR antibody No. 2, synthetic sequence
SEQ ID NO:23=Nucleotide sequence encoding amino acid sequence of the light-chain of humanized anti-hTfR antibody No. 3, synthetic sequence
SEQ ID NO:24=Nucleotide sequence of fusion protein of the heavy-chain of humanized anti-hTfR antibody No. 1 and hI2S, synthetic sequence
SEQ ID NO:25=Nucleotide sequence encoding amino acid sequence of fusion protein of the heavy-chain of humanized anti-hTfR antibody No. 2 and hI2S, synthetic sequence
SEQ ID NO:26=Nucleotide sequence encoding amino acid sequence of fusion protein of the heavy-chain of humanized anti-hTfR antibody No. 3 and hI2S, synthetic sequence
SEQ ID NO:27=Primer Hyg-Sfi5', synthetic sequence
SEQ ID NO:28=Primer Hyg-BstX3', synthetic sequence

The invention claimed is:

1. A method for production of a purified fusion protein in which an anti-human transferrin receptor antibody (anti-hTfR antibody) and a human iduronate-2-sulfatase (human I2S) are fused, the method comprising:
   (a) culturing mammalian cells producing the fusion protein in a serum-free medium to let the mammalian cells secrete the fusion protein in the culture medium,
   (b) collecting culture supernatant by removing the mammalian cells from the culture medium, and
   (c) purifying the fusion protein from the culture supernatant by three column chromatography steps consisting of (i) a column chromatography employing as a solid phase a material to which a substance having affinity for the fusion protein has been bound, (ii) a column chromatography employing as a solid phase a material having affinity for the phosphate group, (iii) and a size exclusion column chromatography, wherein the three column chromatography steps (i) to (iii) are performed sequentially; wherein said anti-hTfR antibody is a humanized antibody, and said humanized anti-hTfR antibody comprises a heavy chain and a light chain and is selected from the group consisting of (d) to (f) below;
   (d) the humanized anti-hTfR antibody, wherein the light chain and the heavy chain have at least 80% amino acid sequence identity to the amino acid sequence set forth as SEQ ID NO:6 and SEQ ID NO:7, respectively,
   (e) the humanized anti-hTfR antibody, wherein the light chain and the heavy chain have at least 80% amino acid sequence identity to the amino acid sequence set forth as SEQ ID NO:8 and SEQ ID NO:9, respectively, and
   (f) the humanized anti-hTfR antibody, wherein the light chain and the heavy chain have at least 80% amino acid sequence identity to the amino acid sequence set forth as SEQ ID NO:10 and SEQ ID NO:11, respectively.

2. The method for production according to claim 1, wherein the substance having affinity for the fusion protein is selected from the group consisting of Protein A, Protein G, Protein L, Protein A/G, an antigen against said antibody, an antibody recognizing said antibody as an antigen, and an antibody against the human I2S.

3. The method for production according to claim 1, wherein the material having affinity for a phosphate group is fluoroapatite or hydroxyapatite.

4. The method for production according to claim 1, wherein the material having affinity for phosphate group is hydroxyapatite.

5. The method for production according to claim 1, wherein said anti-human transferrin receptor antibody and the human I2S are fused via a linker in the fusion protein, and wherein the linker is selected from the group consisting of polyethylene glycol, polypropylene glycol, copolymer of ethylene glycol and propylene glycol, polyoxyethylated polyol, polyvinyl alcohol, polysaccharide, dextran, polyvinyl ether, biodegradable polymer, lipid polymer, chitin, hyaluronic acid, biotin-streptavidin, and a derivative thereof.

6. The method for production according to claim 1, wherein the human I2S is linked, by peptide bonds directly or via a linker sequence, to the heavy chain of said humanized anti-hTfR antibody on the C-terminal side or the N-terminal side of the heavy chain in the fusion protein.

7. The method for production according to claim 6, wherein the linker sequence consists of 1 to 50 amino acid residues.

8. The method for production according to claim 7, wherein the linker sequence comprises an amino acid sequence selected from the group consisting of a single glycine, a single serine, the amino acid sequence of Gly-Ser, the amino acid sequence of Gly-Gly-Ser, the amino acid sequence set forth as SEQ ID NO:1, the amino acid sequence set forth as SEQ ID NO:2, the amino acid sequence set forth as SEQ ID NO:3, and the amino acid sequences consisting of 1 to 10 thereof that are consecutively linked.

9. The method for production according to claim 7, wherein the linker sequence is represented by the amino acid sequence of Gly-Ser.

10. The method for production according to claim 1, wherein the human I2S is linked, by peptide bonds directly or via a linker sequence, to the light chain of said humanized anti-hTfR antibody on the C-terminal side or the N-terminal side of the light chain in the fusion protein.

11. The method for production according to claim 1, wherein the human I2S comprises the amino acid sequence set forth as SEQ ID NO:5.

12. The method for production according to claim 1, wherein the human I2S has at least 80% amino acid sequence identity to the amino acid sequence set forth as SEQ ID NO:5, and has an activity as human I2S.

13. The method for production according to claim 1, wherein the human I2S has at least 90% amino acid sequence identity to the amino acid sequence set forth as SEQ ID NO:5, and has an activity as human I2S.

14. The method for production according to claim 1, wherein the human I2S has the amino acid sequence introduced 1 to 10 amino acid substitutions, deletions or additions relative to the amino acid sequence set forth as SEQ ID NO:5, and has an activity as human I2S.

15. The method for production according to claim 1, wherein the human I2S has the amino acid sequence introduced 1 to 5 amino acid substitutions, deletions or additions relative to the amino acid sequence set forth as SEQ ID NO:5, and has an activity as human I2S.

16. The method for production according to claim 1, wherein the human I2S has the amino acid sequence introduced 1 to 3 amino acid substitutions, deletions or additions relative to the amino acid sequence set forth as SEQ ID NO:5, and has an activity as human I2S.

17. The method for production according to claim 1, wherein the humanized anti-hTfR antibody is selected from the group consisting of (a) to (c) below;
(a) the humanized anti-hTfR antibody, wherein the light chain and the heavy chain thereof comprise the amino acid sequences set forth as SEQ ID NO:6 and SEQ ID NO:7, respectively,
(b) the humanized anti-hTfR antibody, wherein the light chain and the heavy chain thereof comprise the amino acid sequences set forth as SEQ ID NO:8 and SEQ ID NO:9, respectively, and
(c) the humanized anti-hTfR antibody, wherein the light chain and the heavy chain thereof comprise the amino acid sequences set forth as SEQ ID NO:10 and SEQ ID NO:11, respectively.

18. The method for production according to claim 1, the humanized anti-hTfR antibody is selected from the group consisting of (a) to (c) below;
(a) the humanized anti-hTfR antibody, wherein the light chain and the heavy chain thereof have at least 90% amino acid sequence identity to the amino acid sequence set forth as SEQ ID NO:6 and SEQ ID NO:7, respectively,
(b) the humanized anti-hTfR antibody, wherein the light chain and the heavy chain thereof have at least 90% amino acid sequence identity to the amino acid sequence set forth as SEQ ID NO:8 and SEQ ID NO:9, respectively,
(c) the humanized anti-hTfR antibody, wherein the light chain and the heavy chain thereof have at least 90% amino acid sequence identity to the amino acid sequence set forth as SEQ ID NO:10 and SEQ ID NO:11, respectively.

19. The method for production according to claim 1, wherein the humanized anti-hTfR antibody is selected from the group consisting of (a) to (c) below;
(a) the humanized anti-hTfR antibody, wherein the light chain thereof has the amino acid sequence introduced 1 to 10 amino acid substitutions, deletions or additions relative to the amino acid sequence set forth as SEQ ID NO:6, and wherein the heavy chain thereof has the amino acid sequence introduced 1 to 10 amino acid substitutions, deletions or additions relative to the amino acid sequence set forth as SEQ ID NO:7,
(b) the humanized anti-hTfR antibody, wherein the light chain thereof has the amino acid sequence introduced 1 to 10 amino acid substitutions, deletions or additions relative to the amino acid sequence set forth as SEQ ID NO:8, and wherein the heavy chain thereof has the amino acid sequence introduced 1 to 10 amino acid substitutions, deletions or additions relative to the amino acid sequence set forth as SEQ ID NO:9, and
(c) the humanized anti-hTfR antibody, wherein the light chain thereof has the amino acid sequence introduced 1 to 10 amino acid substitutions, deletions or additions relative to the amino acid sequence set forth as SEQ ID NO:10, and wherein the heavy chain thereof has the amino acid sequence introduced 1 to 10 amino acid substitutions, deletions or additions relative to the amino acid sequence set forth as SEQ ID NO:11.

20. The method for production according to claim 1, wherein the humanized anti-hTfR antibody is selected from the group consisting of (a) to (c) below;
(a) the humanized anti-hTfR antibody, wherein the light chain thereof has the amino acid sequence introduced 1 to 3 amino acid substitutions, deletions or additions relative to the amino acid sequence set forth as SEQ ID NO:6, and wherein the heavy chain thereof has the amino acid sequence introduced 1 to 3 amino acid substitutions, deletions or additions relative to the amino acid sequence set forth as SEQ ID NO:7, (b) the humanized anti-hTfR antibody, wherein the light chain thereof has the amino acid sequence introduced 1 to 3 amino acid substitutions, deletions or additions relative to the amino acid sequence set forth as SEQ ID NO:8, and wherein the heavy chain thereof has the amino acid sequence introduced 1 to 3 amino acid substitutions, deletions or additions relative to the amino acid sequence set forth as SEQ ID NO:9, and (c) the humanized anti-hTfR antibody, wherein the light chain thereof has the amino acid sequence introduced 1 to 3 amino acid substitutions, deletions or additions relative to the amino acid sequence set forth as SEQ ID NO:10, and wherein the heavy chain thereof has the amino acid sequence introduced 1 to 3 amino acid substitutions, deletions or additions relative to the amino acid sequence set forth as SEQ ID NO:11.

21. The method for production according to claim 1, wherein the fusion protein is selected from the group consisting of (a) to (c) below;

(a) the fusion protein comprising the light chain of the humanized anti-hTfR antibody having the amino acid sequence set forth as SEQ ID NO:6, and the heavy chain of the humanized anti-hTfR antibody having the amino acid sequence set forth as SEQ ID NO:7 to which the human iduronate-2-sulfatase set forth as SEQ ID NO:5 is linked on the C-terminal side thereof and via a linker sequence of Gly-Ser, (b) the fusion protein comprising the light chain of the humanized anti-hTfR antibody having the amino acid sequence set forth as SEQ ID NO:8, and the heavy chain of the humanized anti-hTfR antibody heavy chain having the amino acid sequence set forth as SEQ ID NO:9 to which the human iduronate-2-sulfatase set forth as SEQ ID NO:5 is linked on the C-terminal side thereof and via a linker sequence of Gly-Ser, and (c) the fusion protein comprising the light chain of the humanized anti-hTfR antibody having the amino acid sequence set forth as SEQ ID NO:10, and the heavy chain of the humanized anti-hTfR antibody having the amino acid sequence set forth as SEQ ID NO:11 to which the human iduronate-2-sulfatase set forth as SEQ ID NO:5 is linked on the C-terminal side thereof and via a linker sequence of Gly-Ser.

22. The method for production according to claim 1, wherein the fusion protein is selected from the group consisting of (a) to (c) below;

(a) the fusion protein comprising;
the light chain of the humanized anti-hTfR antibody having the amino acid sequence set forth as SEQ ID NO:6, and
the heavy chain of the humanized anti-hTfR antibody to which the human iduronate-2-sulfatase is linked on the C-terminal side thereof via a linker sequence of Gly-Ser, and having the amino acid sequence set forth as SEQ ID NO:12 as a whole, (b) the fusion protein comprising;
the light chain of the humanized anti-hTfR antibody having the amino acid sequence set forth as SEQ ID NO:8, and
the heavy chain of the humanized anti-hTfR antibody to which the human iduronate-2-sulfatase is linked on the C-terminal side thereof via a linker sequence of Gly-Ser, and having the amino acid sequence set forth as SEQ ID NO:13 as a whole, (c) the fusion protein comprising;
the light chain of the humanized anti-hTfR antibody has the amino acid sequence set forth as SEQ ID NO:10, and
the heavy chain of the humanized anti-hTfR antibody to which the human iduronate-2-sulfatase is linked on the C-terminal side thereof via a linker sequence of Gly-Ser, and having the amino acid sequence set forth as SEQ ID NO:14 as a whole.

* * * * *

SEQUENCE LISTING

```
<160> NUMBER OF SEQ ID NOS: 28

<210> SEQ ID NO 1
<211> LENGTH: 5
<212> TYPE: PRT
<213> ORGANISM: Artificial Sequence
<220> FEATURE:
<223> OTHER INFORMATION: Amino acid sequence of an exemplified linker 1

<400> SEQUENCE: 1

Gly Gly Gly Gly Ser
1               5

<210> SEQ ID NO 2
<211> LENGTH: 6
<212> TYPE: PRT
<213> ORGANISM: Artificial Sequence
```

```
<220> FEATURE:
<223> OTHER INFORMATION: Amino acid sequence of an exemplified linker 2

<400> SEQUENCE: 2

Gly Gly Gly Gly Gly Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Amino acid sequence of an exemplified linker 3

<400> SEQUENCE: 3

Ser Gly Gly Gly Gly Gly
1               5

<210> SEQ ID NO 4
<211> LENGTH: 760
<212> TYPE: PRT
<213> ORGANISM: Homo sapiens

<400> SEQUENCE: 4

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Leu Tyr Trp Asp Leu Lys
            115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270
```

```
Ser Leu Asn Ala Ile Gly Val Leu Ile Tyr Met Asp Gln Thr Lys Phe
            275                 280                 285

Pro Ile Val Asn Ala Glu Leu Ser Phe Phe Gly His Ala His Leu Gly
        290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
            355                 360                 365

Glu Ser Lys Asn Val Lys Leu Thr Val Ser Asn Val Leu Lys Glu Ile
        370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
        450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
        530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685
```

```
Tyr Val Ser Pro Lys Glu Ser Pro Phe Arg His Val Phe Trp Gly Ser
            690                 695                 700
Gly Ser His Thr Leu Pro Ala Leu Leu Glu Asn Leu Lys Leu Arg Lys
705                 710                 715                 720
Gln Asn Asn Gly Ala Phe Asn Glu Thr Leu Phe Arg Asn Gln Leu Ala
                725                 730                 735
Leu Ala Thr Trp Thr Ile Gln Gly Ala Ala Asn Ala Leu Ser Gly Asp
                740                 745                 750
Val Trp Asp Ile Asp Asn Glu Phe
                755                 760

<210> SEQ ID NO 5
<211> LENGTH: 525
<212> TYPE: PRT
<213> ORGANISM: Homo sapiens

<400> SEQUENCE: 5

Ser Glu Thr Gln Ala Asn Ser Thr Thr Asp Ala Leu Asn Val Leu Leu
1               5                   10                  15
Ile Ile Val Asp Asp Leu Arg Pro Ser Leu Gly Cys Tyr Gly Asp Lys
            20                  25                  30
Leu Val Arg Ser Pro Asn Ile Asp Gln Leu Ala Ser His Ser Leu Leu
        35                  40                  45
Phe Gln Asn Ala Phe Ala Gln Gln Ala Val Cys Ala Pro Ser Arg Val
    50                  55                  60
Ser Phe Leu Thr Gly Arg Arg Pro Asp Thr Thr Arg Leu Tyr Asp Phe
65                  70                  75                  80
Asn Ser Tyr Trp Arg Val His Ala Gly Asn Phe Ser Thr Ile Pro Gln
                85                  90                  95
Tyr Phe Lys Glu Asn Gly Tyr Val Thr Met Ser Val Gly Lys Val Phe
            100                 105                 110
His Pro Gly Ile Ser Ser Asn His Thr Asp Asp Ser Pro Tyr Ser Trp
        115                 120                 125
Ser Phe Pro Pro Tyr His Pro Ser Ser Glu Lys Tyr Glu Asn Thr Lys
    130                 135                 140
Thr Cys Arg Gly Pro Asp Gly Glu Leu His Ala Asn Leu Leu Cys Pro
145                 150                 155                 160
Val Asp Val Leu Asp Val Pro Glu Gly Thr Leu Pro Asp Lys Gln Ser
                165                 170                 175
Thr Glu Gln Ala Ile Gln Leu Leu Glu Lys Met Lys Thr Ser Ala Ser
            180                 185                 190
Pro Phe Phe Leu Ala Val Gly Tyr His Lys Pro His Ile Pro Phe Arg
        195                 200                 205
Tyr Pro Lys Glu Phe Gln Lys Leu Tyr Pro Leu Glu Asn Ile Thr Leu
    210                 215                 220
Ala Pro Asp Pro Glu Val Pro Asp Gly Leu Pro Pro Val Ala Tyr Asn
225                 230                 235                 240
Pro Trp Met Asp Ile Arg Gln Arg Glu Asp Val Gln Ala Leu Asn Ile
                245                 250                 255
Ser Val Pro Tyr Gly Pro Ile Pro Val Asp Phe Gln Arg Lys Ile Arg
            260                 265                 270
Gln Ser Tyr Phe Ala Ser Val Ser Tyr Leu Asp Thr Gln Val Gly Arg
        275                 280                 285
Leu Leu Ser Ala Leu Asp Asp Leu Gln Leu Ala Asn Ser Thr Ile Ile
    290                 295                 300
```

```
Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
        340                 345                 350

Phe Pro Tyr Leu Asp Pro Phe Asp Ser Ala Ser Gln Leu Met Glu Pro
    355                 360                 365

Gly Arg Gln Ser Met Asp Leu Val Glu Leu Val Ser Leu Phe Pro Thr
370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
        420                 425                 430

Arg Glu Leu Ile Ala Tyr Ser Gln Tyr Pro Arg Pro Ser Asp Ile Pro
    435                 440                 445

Gln Trp Asn Ser Asp Lys Pro Ser Leu Lys Asp Ile Lys Ile Met Gly
450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
            485                 490                 495

Leu Tyr Phe Val Asp Ser Asp Pro Leu Gln Asp His Asn Met Tyr Asn
        500                 505                 510

Asp Ser Gln Gly Gly Asp Leu Phe Gln Leu Leu Met Pro
        515                 520                 525

<210> SEQ ID NO 6
<211> LENGTH: 214
<212> TYPE: PRT
<213> ORGANISM: Artificial Sequence
<220> FEATURE:
<223> OTHER INFORMATION: Amino acid sequence of the light-chain of
      humanized anti-hTfR antibody No.1

<400> SEQUENCE: 6

Asp Ile Gln Val Thr Gln Ser Pro Ser Phe Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Phe Gln Gln Lys Pro Gly Lys Ala Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Val Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Arg
            85                  90                  95

Thr Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 7
<211> LENGTH: 446
<212> TYPE: PRT
<213> ORGANISM: Artificial Sequence
<220> FEATURE:
<223> OTHER INFORMATION: Amino acid sequence of the heavy-chain of
      humanized anti-hTfR antibody No.1

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
            20                  25                  30

Gly Met Ser Trp Val Arg Gln Ala Pro Gly Lys Gly Leu Glu Leu Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Asn Asn Arg Tyr Asp Glu Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285
```

```
Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 8
<211> LENGTH: 214
<212> TYPE: PRT
<213> ORGANISM: Artificial Sequence
<220> FEATURE:
<223> OTHER INFORMATION: Amino acid sequence of the light-chain of
      humanized anti-hTfR antibody No.2

<400> SEQUENCE: 8

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asn Asn
            20                  25                  30

Leu Gln Trp Tyr Gln Gln Lys Pro Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Leu Cys Gln Gln Ser Asn Ser Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 9
<211> LENGTH: 453
<212> TYPE: PRT
<213> ORGANISM: Artificial Sequence
<220> FEATURE:
<223> OTHER INFORMATION: Amino acid sequence of the heavy-chain of
      humanized anti-hTfR antibody No.2

<400> SEQUENCE: 9

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asp Tyr
                20                  25                  30

Val Met His Trp Val Arg Gln Ala Pro Gly Gln Gly Leu Glu Trp Ile
            35                  40                  45

Gly Val Ile Ser Thr Tyr Tyr Gly His Gly Ser Tyr Asn Gln Arg Phe
    50                  55                  60

Lys Gly Arg Ala Thr Met Thr Val Asp Lys Ser Ile Ser Thr Ala Tyr
65                  70                  75                  80

Met Glu Leu Val Arg Leu Arg Ser Asp Asp Thr Ala Val Tyr Tyr Cys
                85                  90                  95

Val Arg Gly Gly Tyr Gly Ser Ser Leu Ala Gly Asn Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 10
<211> LENGTH: 219
<212> TYPE: PRT
<213> ORGANISM: Artificial Sequence
<220> FEATURE:
<223> OTHER INFORMATION: Amino acid sequence of the light-chain of
      humanized anti-hTfR antibody No.3

<400> SEQUENCE: 10

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215
```

<210> SEQ ID NO 11
<211> LENGTH: 448
<212> TYPE: PRT
<213> ORGANISM: Artificial Sequence
<220> FEATURE:
<223> OTHER INFORMATION: amino acid sequence of the heavy-chain of humanized anti-hTfR antibody No.3

<400> SEQUENCE: 11

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

```
Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 12
<211> LENGTH: 973
<212> TYPE: PRT
<213> ORGANISM: Artificial Sequence
<220> FEATURE:
<223> OTHER INFORMATION: Amino acid sequence of fusion protein of the
      heavy-chain of humanized anti-hTfR antibody No.1 and hI2S

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
                20                  25                  30

Gly Met Ser Trp Val Arg Gln Ala Pro Gly Lys Gly Leu Glu Leu Val
            35                  40                  45

Ala Asn Ile Asn Thr Asn Gly Gly Ser Thr Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Asn Asn Arg Tyr Asp Glu Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285
```

```
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
            325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly Lys Gly Ser
            435                 440                 445
Ser Glu Thr Gln Ala Asn Ser Thr Thr Asp Ala Leu Asn Val Leu Leu
450                 455                 460
Ile Ile Val Asp Asp Leu Arg Pro Ser Leu Gly Cys Tyr Gly Asp Lys
465                 470                 475                 480
Leu Val Arg Ser Pro Asn Ile Asp Gln Leu Ala Ser His Ser Leu Leu
                485                 490                 495
Phe Gln Asn Ala Phe Ala Gln Ala Val Cys Ala Pro Ser Arg Val
                500                 505                 510
Ser Phe Leu Thr Gly Arg Arg Pro Asp Thr Thr Arg Leu Tyr Asp Phe
            515                 520                 525
Asn Ser Tyr Trp Arg Val His Ala Gly Asn Phe Ser Thr Ile Pro Gln
530                 535                 540
Tyr Phe Lys Glu Asn Gly Tyr Val Thr Met Ser Val Gly Lys Val Phe
545                 550                 555                 560
His Pro Gly Ile Ser Ser Asn His Thr Asp Asp Ser Pro Tyr Ser Trp
                565                 570                 575
Ser Phe Pro Pro Tyr His Pro Ser Ser Glu Lys Tyr Glu Asn Thr Lys
            580                 585                 590
Thr Cys Arg Gly Pro Asp Gly Glu Leu His Ala Asn Leu Leu Cys Pro
            595                 600                 605
Val Asp Val Leu Asp Val Pro Glu Gly Thr Leu Pro Asp Lys Gln Ser
            610                 615                 620
Thr Glu Gln Ala Ile Gln Leu Leu Glu Lys Met Lys Thr Ser Ala Ser
625                 630                 635                 640
Pro Phe Phe Leu Ala Val Gly Tyr His Lys Pro His Ile Pro Phe Arg
                645                 650                 655
Tyr Pro Lys Glu Phe Gln Lys Leu Tyr Pro Leu Glu Asn Ile Thr Leu
            660                 665                 670
Ala Pro Asp Pro Glu Val Pro Asp Gly Leu Pro Pro Val Ala Tyr Asn
            675                 680                 685
Pro Trp Met Asp Ile Arg Gln Arg Glu Asp Val Gln Ala Leu Asn Ile
690                 695                 700
```

Ser Val Pro Tyr Gly Pro Ile Pro Val Asp Phe Gln Arg Lys Ile Arg
705                 710                 715                 720

Gln Ser Tyr Phe Ala Ser Val Ser Tyr Leu Asp Thr Gln Val Gly Arg
            725                 730                 735

Leu Leu Ser Ala Leu Asp Asp Leu Gln Leu Ala Asn Ser Thr Ile Ile
                740                 745                 750

Ala Phe Thr Ser Asp His Gly Trp Ala Leu Gly Glu His Gly Glu Trp
        755                 760                 765

Ala Lys Tyr Ser Asn Phe Asp Val Ala Thr His Val Pro Leu Ile Phe
770                 775                 780

Tyr Val Pro Gly Arg Thr Ala Ser Leu Pro Glu Ala Gly Glu Lys Leu
785                 790                 795                 800

Phe Pro Tyr Leu Asp Pro Phe Asp Ser Ala Ser Gln Leu Met Glu Pro
            805                 810                 815

Gly Arg Gln Ser Met Asp Leu Val Glu Leu Val Ser Leu Phe Pro Thr
                820                 825                 830

Leu Ala Gly Leu Ala Gly Leu Gln Val Pro Pro Arg Cys Pro Val Pro
        835                 840                 845

Ser Phe His Val Glu Leu Cys Arg Glu Gly Lys Asn Leu Leu Lys His
850                 855                 860

Phe Arg Phe Arg Asp Leu Glu Glu Asp Pro Tyr Leu Pro Gly Asn Pro
865                 870                 875                 880

Arg Glu Leu Ile Ala Tyr Ser Gln Tyr Pro Arg Pro Ser Asp Ile Pro
            885                 890                 895

Gln Trp Asn Ser Asp Lys Pro Ser Leu Lys Asp Ile Lys Ile Met Gly
                900                 905                 910

Tyr Ser Ile Arg Thr Ile Asp Tyr Arg Tyr Thr Val Trp Val Gly Phe
        915                 920                 925

Asn Pro Asp Glu Phe Leu Ala Asn Phe Ser Asp Ile His Ala Gly Glu
930                 935                 940

Leu Tyr Phe Val Asp Ser Asp Pro Leu Gln Asp His Asn Met Tyr Asn
945                 950                 955                 960

Asp Ser Gln Gly Gly Asp Leu Phe Gln Leu Leu Met Pro
            965                 970

<210> SEQ ID NO 13
<211> LENGTH: 980
<212> TYPE: PRT
<213> ORGANISM: Artificial Sequence
<220> FEATURE:
<223> OTHER INFORMATION: Amino acid sequence of fusion protein of the
      heavy-chain of humanized anti-hTfR antibody No.2 and hI2S

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Ile
        35                  40                  45

Gly Val Ile Ser Thr Tyr Tyr Gly His Gly Ser Tyr Asn Gln Arg Phe
    50                  55                  60

Lys Gly Arg Ala Thr Met Thr Val Asp Lys Ser Ile Ser Thr Ala Tyr
65                  70                  75                  80

Met Glu Leu Val Arg Leu Arg Ser Asp Asp Thr Ala Val Tyr Tyr Cys
                85                  90                  95

```
Val Arg Gly Gly Tyr Gly Ser Ser Ser Leu Ala Gly Asn Phe Asp Val
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys Gly Ser Ser Glu Thr Gln Ala Asn Ser Thr Thr
            450                 455                 460

Asp Ala Leu Asn Val Leu Leu Ile Ile Val Asp Asp Leu Arg Pro Ser
465                 470                 475                 480

Leu Gly Cys Tyr Gly Asp Lys Leu Val Arg Ser Pro Asn Ile Asp Gln
                485                 490                 495

Leu Ala Ser His Ser Leu Leu Phe Gln Asn Ala Phe Ala Gln Gln Ala
            500                 505                 510
```

```
Val Cys Ala Pro Ser Arg Val Ser Phe Leu Thr Gly Arg Pro Asp
        515                 520                 525

Thr Thr Arg Leu Tyr Asp Phe Asn Ser Tyr Trp Arg Val His Ala Gly
530                 535                 540

Asn Phe Ser Thr Ile Pro Gln Tyr Phe Lys Glu Asn Gly Tyr Val Thr
545                 550                 555                 560

Met Ser Val Gly Lys Val Phe His Pro Gly Ile Ser Ser Asn His Thr
                565                 570                 575

Asp Asp Ser Pro Tyr Ser Trp Ser Phe Pro Pro Tyr His Pro Ser Ser
                580                 585                 590

Glu Lys Tyr Glu Asn Thr Lys Thr Cys Arg Gly Pro Asp Gly Glu Leu
            595                 600                 605

His Ala Asn Leu Leu Cys Pro Val Asp Val Leu Asp Val Pro Glu Gly
        610                 615                 620

Thr Leu Pro Asp Lys Gln Ser Thr Glu Gln Ala Ile Gln Leu Leu Glu
625                 630                 635                 640

Lys Met Lys Thr Ser Ala Ser Pro Phe Leu Ala Val Gly Tyr His
                645                 650                 655

Lys Pro His Ile Pro Phe Arg Tyr Pro Lys Glu Phe Gln Lys Leu Tyr
                660                 665                 670

Pro Leu Glu Asn Ile Thr Leu Ala Pro Asp Pro Glu Val Pro Asp Gly
            675                 680                 685

Leu Pro Pro Val Ala Tyr Asn Pro Trp Met Asp Ile Arg Gln Arg Glu
        690                 695                 700

Asp Val Gln Ala Leu Asn Ile Ser Val Pro Tyr Gly Pro Ile Pro Val
705                 710                 715                 720

Asp Phe Gln Arg Lys Ile Arg Gln Ser Tyr Phe Ala Ser Val Ser Tyr
                725                 730                 735

Leu Asp Thr Gln Val Gly Arg Leu Leu Ser Ala Leu Asp Asp Leu Gln
            740                 745                 750

Leu Ala Asn Ser Thr Ile Ile Ala Phe Thr Ser Asp His Gly Trp Ala
        755                 760                 765

Leu Gly Glu His Gly Glu Trp Ala Lys Tyr Ser Asn Phe Asp Val Ala
    770                 775                 780

Thr His Val Pro Leu Ile Phe Tyr Val Pro Gly Arg Thr Ala Ser Leu
785                 790                 795                 800

Pro Glu Ala Gly Glu Lys Leu Phe Pro Tyr Leu Asp Pro Phe Asp Ser
                805                 810                 815

Ala Ser Gln Leu Met Glu Pro Gly Arg Gln Ser Met Asp Leu Val Glu
            820                 825                 830

Leu Val Ser Leu Phe Pro Thr Leu Ala Gly Leu Ala Gly Leu Gln Val
        835                 840                 845

Pro Pro Arg Cys Pro Val Pro Ser Phe His Val Glu Leu Cys Arg Glu
    850                 855                 860

Gly Lys Asn Leu Leu Lys His Phe Arg Phe Arg Asp Leu Glu Glu Asp
865                 870                 875                 880

Pro Tyr Leu Pro Gly Asn Pro Arg Glu Leu Ile Ala Tyr Ser Gln Tyr
                885                 890                 895

Pro Arg Pro Ser Asp Ile Pro Gln Trp Asn Ser Asp Lys Pro Ser Leu
            900                 905                 910

Lys Asp Ile Lys Ile Met Gly Tyr Ser Ile Arg Thr Ile Asp Tyr Arg
        915                 920                 925
```

Tyr Thr Val Trp Val Gly Phe Asn Pro Asp Glu Phe Leu Ala Asn Phe
            930             935             940

Ser Asp Ile His Ala Gly Glu Leu Tyr Phe Val Asp Ser Asp Pro Leu
945             950             955             960

Gln Asp His Asn Met Tyr Asn Asp Ser Gln Gly Gly Asp Leu Phe Gln
                965             970             975

Leu Leu Met Pro
            980

<210> SEQ ID NO 14
<211> LENGTH: 975
<212> TYPE: PRT
<213> ORGANISM: Artificial Sequence
<220> FEATURE:
<223> OTHER INFORMATION: Amino acid sequence of fusion protein of the
      heavy-chain of humanized anti-hTfR antibody No.3 and hI2S

<400> SEQUENCE: 14

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

Gly Ser Ser Glu Thr Gln Ala Asn Ser Thr Thr Asp Ala Leu Asn Val
450                 455                 460

Leu Leu Ile Ile Val Asp Asp Leu Arg Pro Ser Leu Gly Cys Tyr Gly
465                 470                 475                 480

Asp Lys Leu Val Arg Ser Pro Asn Ile Asp Gln Leu Ala Ser His Ser
                485                 490                 495

Leu Leu Phe Gln Asn Ala Phe Ala Gln Gln Ala Val Cys Ala Pro Ser
                500                 505                 510

Arg Val Ser Phe Leu Thr Gly Arg Arg Pro Asp Thr Thr Arg Leu Tyr
                515                 520                 525

Asp Phe Asn Ser Tyr Trp Arg Val His Ala Gly Asn Phe Ser Thr Ile
            530                 535                 540

Pro Gln Tyr Phe Lys Glu Asn Gly Tyr Val Thr Met Ser Val Gly Lys
545                 550                 555                 560

Val Phe His Pro Gly Ile Ser Ser Asn His Thr Asp Asp Ser Pro Tyr
                565                 570                 575

Ser Trp Ser Phe Pro Pro Tyr His Pro Ser Ser Glu Lys Tyr Glu Asn
                580                 585                 590

Thr Lys Thr Cys Arg Gly Pro Asp Gly Glu Leu His Ala Asn Leu Leu
            595                 600                 605

Cys Pro Val Asp Val Leu Asp Val Pro Glu Gly Thr Leu Pro Asp Lys
            610                 615                 620

Gln Ser Thr Glu Gln Ala Ile Gln Leu Leu Glu Lys Met Lys Thr Ser
625                 630                 635                 640

Ala Ser Pro Phe Phe Leu Ala Val Gly Tyr His Lys Pro His Ile Pro
                645                 650                 655

Phe Arg Tyr Pro Lys Glu Phe Gln Lys Leu Tyr Pro Leu Glu Asn Ile
                660                 665                 670

Thr Leu Ala Pro Asp Pro Glu Val Pro Asp Gly Leu Pro Pro Val Ala
            675                 680                 685

Tyr Asn Pro Trp Met Asp Ile Arg Gln Arg Glu Asp Val Gln Ala Leu
690                 695                 700

Asn Ile Ser Val Pro Tyr Gly Pro Ile Pro Val Asp Phe Gln Arg Lys
705                 710                 715                 720
```

Ile Arg Gln Ser Tyr Phe Ala Ser Val Ser Tyr Leu Asp Thr Gln Val
            725                 730                 735

Gly Arg Leu Leu Ser Ala Leu Asp Asp Leu Gln Leu Ala Asn Ser Thr
        740                 745                 750

Ile Ile Ala Phe Thr Ser Asp His Gly Trp Ala Leu Gly Glu His Gly
        755                 760                 765

Glu Trp Ala Lys Tyr Ser Asn Phe Asp Val Ala Thr His Val Pro Leu
        770                 775                 780

Ile Phe Tyr Val Pro Gly Arg Thr Ala Ser Leu Pro Glu Ala Gly Glu
785                 790                 795                 800

Lys Leu Phe Pro Tyr Leu Asp Pro Phe Asp Ser Ala Ser Gln Leu Met
            805                 810                 815

Glu Pro Gly Arg Gln Ser Met Asp Leu Val Glu Leu Val Ser Leu Phe
        820                 825                 830

Pro Thr Leu Ala Gly Leu Ala Gly Leu Gln Val Pro Pro Arg Cys Pro
        835                 840                 845

Val Pro Ser Phe His Val Glu Leu Cys Arg Glu Gly Lys Asn Leu Leu
        850                 855                 860

Lys His Phe Arg Phe Arg Asp Leu Glu Glu Asp Pro Tyr Leu Pro Gly
865                 870                 875                 880

Asn Pro Arg Glu Leu Ile Ala Tyr Ser Gln Tyr Pro Arg Pro Ser Asp
            885                 890                 895

Ile Pro Gln Trp Asn Ser Asp Lys Pro Ser Leu Lys Asp Ile Lys Ile
        900                 905                 910

Met Gly Tyr Ser Ile Arg Thr Ile Asp Tyr Arg Tyr Thr Val Trp Val
        915                 920                 925

Gly Phe Asn Pro Asp Glu Phe Leu Ala Asn Phe Ser Asp Ile His Ala
        930                 935                 940

Gly Glu Leu Tyr Phe Val Asp Ser Asp Pro Leu Gln Asp His Asn Met
945                 950                 955                 960

Tyr Asn Asp Ser Gln Gly Gly Asp Leu Phe Gln Leu Leu Met Pro
            965                 970                 975

<210> SEQ ID NO 15
<211> LENGTH: 107
<212> TYPE: PRT
<213> ORGANISM: Artificial Sequence
<220> FEATURE:
<223> OTHER INFORMATION: Amino acid sequence of the light-chain variable
      region of humanized anti-hTfR antibody No.1

<400> SEQUENCE: 15

Asp Ile Gln Val Thr Gln Ser Pro Ser Phe Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Phe Gln Gln Lys Pro Gly Lys Ala Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Val Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Arg
            85                  90                  95

Thr Phe Gly Gly Gly Thr Lys Val Glu Ile Lys
            100                 105

<210> SEQ ID NO 16
<211> LENGTH: 116
<212> TYPE: PRT
<213> ORGANISM: Artificial Sequence
<220> FEATURE:
<223> OTHER INFORMATION: Amino acid sequence of the heavy-chain variable
      region of humanized anti-hTfR antibody No.1

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
            20                  25                  30

Gly Met Ser Trp Val Arg Gln Ala Pro Gly Lys Gly Leu Glu Leu Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Asn Asn Arg Tyr Asp Glu Asp Tyr Trp Gly Gln Gly Thr Leu Val
            100                 105                 110

Thr Val Ser Ser
        115

<210> SEQ ID NO 17
<211> LENGTH: 107
<212> TYPE: PRT
<213> ORGANISM: Artificial Sequence
<220> FEATURE:
<223> OTHER INFORMATION: Amino acid sequence of the light-chain variable
      region of humanized anti-hTfR antibody No.2

<400> SEQUENCE: 17

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asn Asn
            20                  25                  30

Leu Gln Trp Tyr Gln Gln Lys Pro Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Leu Cys Gln Gln Ser Asn Ser Trp Pro Arg
                85                  90                  95

Thr Phe Gly Gln Gly Thr Lys Val Glu Ile Lys
            100                 105

<210> SEQ ID NO 18
<211> LENGTH: 120
<212> TYPE: PRT
<213> ORGANISM: Artificial Sequence
<220> FEATURE:
<223> OTHER INFORMATION: Amino acid sequence of the heavy-chain variable
      region of humanized anti-hTfR antibody No.2

```
<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Ile
        35                  40                  45

Gly Val Ile Ser Thr Tyr Tyr Gly His Gly Ser Tyr Asn Gln Arg Phe
    50                  55                  60

Lys Gly Arg Ala Thr Met Thr Val Asp Lys Ser Ile Ser Thr Ala Tyr
65                  70                  75                  80

Met Glu Leu Val Arg Leu Arg Ser Asp Asp Thr Ala Val Tyr Tyr Cys
                85                  90                  95

Val Arg Gly Gly Tyr Gly Ser Ser Leu Ala Gly Asn Phe Asp Val
            100                 105                 110

Trp Gly Gln Gly Thr Thr Val Thr
        115                 120

<210> SEQ ID NO 19
<211> LENGTH: 112
<212> TYPE: PRT
<213> ORGANISM: Artificial Sequence
<220> FEATURE:
<223> OTHER INFORMATION: Amino acid sequence of the light-chain variable
      region of humanized anti-hTfR antibody No.3

<400> SEQUENCE: 19

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

<210> SEQ ID NO 20
<211> LENGTH: 118
<212> TYPE: PRT
<213> ORGANISM: Artificial Sequence
<220> FEATURE:
<223> OTHER INFORMATION: Amino acid sequence of the heavy-chain variable
      region of humanized anti-hTfR antibody No.3

<400> SEQUENCE: 20

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45
```

-continued

```
Gly Asp Ile Tyr Pro Gly Gly Asp Tyr Pro Thr Tyr Ser Glu Lys Phe
 50                  55                  60
Lys Val Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Ser Gly Asn Tyr Asp Glu Val Ala Tyr Trp Gly Gln Gly Thr
            100                 105                 110
Leu Val Thr Val Ser Ser
        115
```

<210> SEQ ID NO 21
<211> LENGTH: 725
<212> TYPE: DNA
<213> ORGANISM: Artificial Sequence
<220> FEATURE:
<223> OTHER INFORMATION: Nucleotide seuquence encoding amino acid
      sequence of the light-chain of humanized anti-hTfR antibody No.1,
      synthetic sequence

<400> SEQUENCE: 21

```
acgcgtgccg ccaccatggg ctggagctgg attctgctgt tcctcctgag cgtgacagca      60
ggagtgcaca gcgacatcca ggtcacacag tcaccaagtt ttctgagcgc aagcgtgggc     120
gacagggtca ctatcacatg caaggcaagc caggacgtga actccgcagt ggcctggttc     180
cagcagaagc cagggaaagc acccaagctg ctgatctatt ggacctctac aaggcacacc     240
ggtgtcccag atcggttctc aggttccggc agcggaacag tgtatactct gaccatttcc     300
agcctgcagc ctgaagactt cgctacttac tattgccagc agcattactc caccccaaga     360
acatttggcg agggactaaa gtggagatca agaggaccgt ggccgctccc tccgtcttc     420
attttcccc ctagcgacga acagctgaag agtggcacag cctcagtggt ctgtctgctg     480
aacaatttct accctaggga ggctaaagtg cagtggaagg tcgataacgc actgcagtct     540
ggaaatagtc aggagtcagt gacagaacag gactccaaag atagcactta ttctctgtct     600
agtacactga ctctgagcaa ggccgattac gaaaagcaca agtgtatgc ttgcgaagtc     660
acccatcagg ggctgtcatc accagtcacc aagtcattca atagaggcga gtgctaagcg     720
gccgc                                                                725
```

<210> SEQ ID NO 22
<211> LENGTH: 725
<212> TYPE: PRT
<213> ORGANISM: Artificial Sequence
<220> FEATURE:
<223> OTHER INFORMATION: Nucleotide seuquence encoding amino acid
      sequence of the light-chain of humanized anti-hTfR antibody No.2,
      synthetic sequence

<400> SEQUENCE: 22

```
Ala Cys Gly Cys Gly Thr Gly Cys Cys Gly Cys Cys Ala Cys Cys Ala
  1               5                  10                  15
Thr Gly Gly Gly Cys Thr Gly Gly Ala Gly Cys Thr Gly Gly Ala Thr
                 20                  25                  30
Thr Cys Thr Gly Cys Thr Gly Thr Thr Cys Cys Thr Cys Cys Thr Gly
            35                  40                  45
Ala Gly Cys Gly Thr Gly Ala Cys Ala Gly Cys Ala Gly Gly Ala Gly
        50                  55                  60
Thr Gly Cys Ala Cys Ala Gly Cys Gly Ala Cys Ala Thr Cys Cys Ala
 65                  70                  75                  80
```

-continued

```
Gly Cys Thr Gly Ala Cys Cys Ala Gly Thr Cys Cys Cys
                85              90              95
Gly Ala Thr Thr Thr Cys Cys Ala Gly Thr Cys Cys Gly Thr Gly Ala
            100             105             110
Cys Cys Cys Cys Cys Ala Ala Gly Gly Ala Gly Ala Ala Ala Gly Thr
        115             120             125
Cys Ala Cys Cys Ala Thr Cys Ala Cys Ala Thr Gly Cys Ala Gly Ala
    130             135             140
Gly Cys Ala Thr Cys Ala Cys Ala Gly Thr Cys Cys Ala Thr Thr Ala
145             150             155             160
Gly Cys Ala Ala Cys Ala Ala Thr Cys Thr Gly Cys Ala Gly Thr Gly
            165             170             175
Gly Thr Ala Cys Cys Ala Gly Cys Ala Gly Ala Ala Gly Cys Cys Ala
            180             185             190
Gly Ala Cys Cys Ala Gly Ala Gly Cys Cys Cys Ala Ala Gly Cys
    195             200             205
Thr Gly Cys Thr Gly Ala Thr Cys Ala Ala Ala Thr Ala Thr Gly Cys
    210             215             220
Cys Thr Cys Thr Cys Ala Gly Ala Gly Thr Ala Thr Thr Thr Cys Ala
225             230             235             240
Gly Gly Cys Ala Thr Ala Cys Cys Thr Thr Cys Thr Ala Gly Gly Thr
            245             250             255
Thr Cys Thr Cys Cys Gly Gly Thr Ala Gly Cys Gly Gly Cys Thr Cys
        260             265             270
Thr Gly Gly Ala Ala Cys Cys Gly Ala Cys Thr Thr Ala Cys Thr
    275             280             285
Cys Thr Gly Ala Cys Cys Ala Thr Cys Ala Ala Cys Ala Gly Thr Cys
    290             295             300
Thr Gly Gly Ala Gly Gly Cys Thr Gly Ala Ala Gly Ala Thr Gly Cys
305             310             315             320
Cys Gly Cys Thr Ala Cys Ala Thr Ala Cys Thr Thr Gly Thr Gly Cys
            325             330             335
Cys Ala Gly Cys Ala Gly Ala Gly Thr Ala Thr Thr Cys Ala Thr
            340             345             350
Gly Gly Cys Cys Thr Ala Gly Gly Ala Cys Cys Thr Thr Thr Gly Gly
        355             360             365
Cys Cys Ala Gly Gly Gly Ala Cys Ala Ala Ala Gly Gly Thr Gly
370             375             380
Gly Ala Gly Ala Thr Cys Ala Ala Ala Gly Gly Ala Cys Thr Gly
385             390             395             400
Thr Gly Gly Cys Ala Gly Cys Cys Cys Cys Ala Ala Gly Thr Cys
        405             410             415
Cys Thr Thr Cys Ala Thr Thr Thr Thr Cys Cys Cys Cys Thr
        420             425             430
Thr Cys Ala Gly Ala Cys Gly Ala Ala Cys Ala Gly Cys Thr Gly Ala
    435             440             445
Ala Gly Ala Gly Cys Gly Gly Cys Ala Cys Ala Gly Cys Ala Thr Cys
450             455             460
Thr Gly Thr Gly Gly Thr Cys Thr Gly Thr Gly Cys Thr Gly
465             470             475             480
Ala Ala Cys Ala Ala Thr Thr Cys Thr Ala Cys Cys Ala Cys
            485             490             495
```

Gly Gly Gly Ala Gly Gly Cys Thr Ala Ala Gly Thr Gly Cys Ala
                500                 505                 510
Gly Thr Gly Gly Ala Ala Gly Thr Cys Gly Ala Thr Ala Ala Cys
            515                 520                 525
Gly Cys Ala Cys Thr Gly Cys Ala Gly Thr Cys Cys Gly Gly Ala Ala
        530                 535                 540
Ala Thr Ala Gly Cys Cys Ala Gly Gly Ala Gly Thr Cys Thr Gly Thr
545                 550                 555                 560
Gly Ala Cys Thr Gly Ala Ala Cys Ala Gly Ala Cys Ala Gly Thr
            565                 570                 575
Ala Ala Gly Gly Ala Thr Thr Cys Ala Ala Cys Cys Thr Ala Thr Thr
            580                 585                 590
Cys Cys Cys Thr Gly Thr Cys Ala Gly Cys Ala Cys Ala Cys Thr
        595                 600                 605
Gly Ala Cys Thr Cys Thr Gly Ala Cys Ala Ala Ala Gly Cys Cys
        610                 615                 620
Gly Ala Thr Thr Ala Cys Gly Ala Gly Ala Ala Gly Cys Ala Cys Ala
625                 630                 635                 640
Ala Ala Gly Thr Gly Thr Ala Thr Gly Cys Thr Thr Gly Cys Gly Ala
            645                 650                 655
Ala Gly Thr Cys Ala Cys Ala Cys Ala Thr Cys Ala Gly Gly Gly
        660                 665                 670
Cys Thr Gly Thr Cys Thr Ala Gly Thr Cys Cys Cys Gly Thr Gly Ala
            675                 680                 685
Cys Thr Ala Ala Gly Thr Cys Thr Thr Thr Thr Ala Ala Thr Ala Gly
            690                 695                 700
Gly Gly Gly Thr Gly Ala Ala Thr Gly Thr Thr Ala Ala Gly Cys Gly
705                 710                 715                 720
Gly Cys Cys Gly Cys
            725

<210> SEQ ID NO 23
<211> LENGTH: 740
<212> TYPE: DNA
<213> ORGANISM: Artificial Sequence
<220> FEATURE:
<223> OTHER INFORMATION: Nucleotide seuquence encoding amino acid
      sequence of the light-chain of humanized anti-hTfR antibody No.3,
      synthetic sequence

<400> SEQUENCE: 23
acgcgtgccg ccaccatggg ctggagctgg attctgctgt tcctcctgag cgtgacagca      60
ggagtgcaca gcgacatcgt gatgacccag actcccctga gcctgagcgt gacacctggc     120
cagcctgcca gcatcagctg cagaagctct cagagcctgg tgcacagcaa cggcaacacc     180
tacctgcact ggtatctgca gaagcccggc cagagccctc agctgctgat ctacaaggtg     240
tccaacagat tcagcggcgt gcccgacaga ttctccggca gcggctctgg caccgacttc     300
accctgaaga tttccagagt ggaagccgag gacgtgggcg tgtactactg cagccagagc     360
acccacgtgc ctggacattt cggccagggc accaaggtgg aaatcaagag aaccgtggcc     420
gctcccagcg tgttcatctt cccacctagc gacgagcagc tgaagtccgg cacagcctct     480
gtcgtgtgcc tgctgaacaa cttctacccc cgcgaggcca aggtgcagtg gaaggtggac     540
aacgccctgc agagcggcaa cagccaggaa agcgtgaccg agcaggactc caaggacagc     600
acctacagcc tgagcagcac cctgaccctg agcaaggccg actacgagaa gcacaaggtg     660

| | |
|---|---|
| tacgcctgcg aagtgaccca ccagggcctg tctagccccg tgaccaagag cttcaacaga | 720 |
| ggcgagtgct aagcggccgc | 740 |

<210> SEQ ID NO 24
<211> LENGTH: 3002
<212> TYPE: DNA
<213> ORGANISM: Artificial Sequence
<220> FEATURE:
<223> OTHER INFORMATION: Nucleotide seuquence encoding amino acid
      sequence of fusion protein of the heavy-chain of humanized anti-
      hTfR antibody No.1 and hI2S, synthetic sequence

<400> SEQUENCE: 24

| | |
|---|---|
| acgcgtgccg ccaccatggg ctggagctgg attctgctgt tcctcctgag cgtgacagca | 60 |
| ggagtgcaca gcgaagtgca gctggtcgaa tcagggggg gctggtgca gcctggaggc | 120 |
| agcctgagac tgtcctgcgc cgcttctggc ttgacctta gcaactacgg gatgtcctgg | 180 |
| gtgcggcagg ctcctggcaa gggactggag ttggtggcca acatcaatac caacggcgga | 240 |
| agtacatact atcccgattc agtgaagggc cggttcacca tcagcaggga caacgccaag | 300 |
| aacagcctgt atctgcagat gaactctctg agggccgagg atacagccgt gtactattgc | 360 |
| actaacaacc ggtacgacga ggactattgg ggccagggca ccctggtgac agtgtctagc | 420 |
| gcctctacca agggcccaag cgtgtttcct ctggctccat cctctaaatc cacctctggc | 480 |
| ggcacagccg ctctgggctg tctggtgaag gattacttcc cagagcccgt gacagtgtct | 540 |
| tggaacagcg gcgccctgac ctccggcgtg cacacatttc ctgctgtgct gcagagctcc | 600 |
| ggcctgtaca gcctgtctag cgtggtgacc gtgccatcct ctagcctggg cacccagaca | 660 |
| tatatctgca acgtgaatca caagcccagc aatacaaagg tggataagaa ggtggagcca | 720 |
| aagtcctgtg acaagaccca catgtgcccc ccttgtcctg ctccagagct gctgggagga | 780 |
| ccaagcgtgt tcctgtttcc acccaagccc aaggataccc tgatgatctc tcggaccccc | 840 |
| gaggtgacat gcgtggtggt ggatgtgagc acgaggaccc cgaggtgaa gttcaactgg | 900 |
| tatgtggacg gcgtggaggt gcacaatgct aagaccaagc ccagggagga gcagtacaac | 960 |
| tccacctata gagtggtgtc tgtgctgaca gtgctgcacc aggattggct gaacggcaag | 1020 |
| gagtataagt gcaaggtgtc caataaggcc ctgccccgctc ctatcgagaa gaccatctct | 1080 |
| aaggccaagg gccagcccag agagcctcag gtgtacacac tgcctccatc ccgggatgag | 1140 |
| ctgaccaaga accaggtgtc tctgacatgt ctggtcaagg gcttctatcc ctctgacatc | 1200 |
| gccgtggagt gggagagcaa tggccagcct gagacaatt acaagaccac ccccctgtg | 1260 |
| ctggattccg acggctcttt ctttctgtat agcaagctga ccgtggacaa gtcccggtgg | 1320 |
| cagcagggca cgtgttcag ctgttccgtg atgcacgaag ctctgcataa tcactatact | 1380 |
| cagaaatccc tgtcactgtc acctggtaaa ggatcttccg aaacgcaggc caactcgacc | 1440 |
| acagatgctc tgaacgttct tctcatcatc gtggatgacc tgcgcccctc cctgggctgt | 1500 |
| tatgggata agctggtgag gtccccaaat attgaccaac tggcatccca cagcctcctc | 1560 |
| ttccagaatg cctttgcgca gcaagcagtg tgcgccccga gccgcgtttc tttcctcact | 1620 |
| ggcaggagac ctgacaccac ccgcctgtac gacttcaact cctactggag ggtgcacgct | 1680 |
| ggaaacttct ccaccatccc ccagtacttc aaggagaatg gctatgtgac catgtcggtg | 1740 |
| ggaaaagtct ttcaccctgg gatatcttct aaccataccg atgattctcc gtatagctgg | 1800 |
| tcttttccac cttatcatcc ttcctctgag aagtatgaaa acactaagac atgtcgaggg | 1860 |
| ccagatggag aactccatgc caacctgctt tgccctgtgg atgtgctgga tgttcccgag | 1920 |

```
ggcaccttgc ctgacaaaca gagcactgag caagccatac agttgttgga aaagatgaaa    1980
acgtcagcca gtcctttctt cctggccgtt gggtatcata agccacacat ccccttcaga    2040
taccccaagg aatttcagaa gttgtatccc ttggagaaca tcaccctggc ccccgatccc    2100
gaggtccctg atggcctacc ccctgtggcc tacaacccct ggatggacat caggcaacgg    2160
gaagacgtcc aagccttaaa catcagtgtg ccgtatggtc caattcctgt ggactttcag    2220
cggaaaatcc gccagagcta ctttgcctct gtgtcatatt tggatacaca ggtcggccgc    2280
ctcttgagtg ctttggacga tcttcagctg ccaacagca ccatcattgc atttacctcg     2340
gatcatgggt gggctctagg tgaacatgga gaatgggcca atacagcaa ttttgatgtt     2400 gctacccatg ttcccctgat attctatgtt cctggaagga cggcttcact tccggaggca    2460
ggcgagaagc ttttccctta cctcgaccct tttgattccg cctcacagtt gatggagcca    2520
ggcaggcaat ccatggacct tgtggaactt gtgtctcttt ttcccacgct ggctggactt    2580
gcaggactgc aggttccacc tcgctgcccc gttccttcat ttcacgttga gctgtgcaga    2640
gaaggcaaga accttctgaa gcattttcga ttccgtgact tggaagaaga tccgtacctc    2700
cctggtaatc cccgtgaact gattgcctat agccagtatc cccggccttc agacatccct    2760
cagtggaatt ctgacaagcc gagttttaaaa gatataaaga tcatgggcta ttccatacgc    2820
accatagact ataggtatac tgtgtgggtt ggcttcaatc ctgatgaatt tctagctaac    2880
ttttctgaca tccatgcagg ggaactgtat tttgtggatt ctgacccatt gcaggatcac    2940
aatatgtata atgattccca aggtggagac cttttccagt tgttgatgcc ttaagcggcc    3000
gc                                                                   3002

<210> SEQ ID NO 25
<211> LENGTH: 3023
<212> TYPE: DNA
<213> ORGANISM: Artificial Sequence
<220> FEATURE:
<223> OTHER INFORMATION: Nucleotide seuquence encoding amino acid
      sequence of fusion protein of the heavy-chain of humanized anti-
      hTfR antibody No.2 and hI2S, synthetic sequence

<400> SEQUENCE: 25
acgcgtgccg ccaccatggg ctggagctgg attctgctgt tcctcctgag cgtgacagca    60
ggagtgcaca gccaggtgca gctggtccag tcaggagccg aagtgaaaaa gcccggagcc    120
tcagtcaaag tgtcttgtaa agcatcaggt tatacattta cagactacgt catgcactgg    180
gtgaggcagg cacctggaca gggtctggaa tggatcggcg tgatctccac ttactatggc    240
catggaagct acaaccagag attcaagggc agggcgacaa tgactgtaga caaatcaatt    300
tccactgctt atatggagct ggtaaggctg cggtccgacg ataccgctgt gtactattgc    360
gtacgaggag atacggctc cagctctctg gctggtaatt tcgatgtgtg ggggcagggt     420
accacagtca ccgtgagttc agcaagcaca aagggcccat ctgtgtttcc actggccccc    480
tccagcaaaa gcacctctgg gggtacagcc gctctggat gtctggtgaa ggattatttc     540
ccagagccag tcaccgtgtc ctggaacagc ggagccctga catctggagt ccacactttt    600
ccagctgtgc tgcagtctag tgggctgtac tccctgtcat ccgtggtcac tgtccccagc    660
tctagtctgg gtacccagac atatatctgc aacgtgaatc acaagccatc taataccaaa    720
gtcgacaaga aagtggaacc caagtcctgt gataaaactc atacctgccc ccccttgtcct   780 gcaccagagc tgctggaggg accatccgtg ttcctgtttc cacccaagcc taagacacc     840 ctgatgatta gccgaactcc cgaagtcacc tgcgtggtcg tggacgtgtc tcacgaggac    900
```

-continued

```
cctgaagtca agtttaactg gtacgtggat ggcgtcgagg tgcataatgc taagacaaaa    960
ccccgagagg aacagtacaa cagtacatat cgtgtcgtgt cagtgctgac cgtcctgcat   1020
caggactggc tgaacgggaa ggaatataag tgcaaagtgt ccaataaggc actgcccgcc   1080
cctatcgaga aaaccattag caaggccaaa ggacagccta gggaaccaca ggtgtacaca   1140
ctgcctccat cccgggacga gctgactaag aaccaggtca gcctgacctg tctggtgaaa   1200
ggcttctatc cttcagatat cgctgtggag tgggaaagta atggacagcc agagaacaat   1260
tacaagacta ccccccctgt gctggactct gatgggagtt tctttctgta ttctaagctg   1320
accgtggata aaagtcggtg gcagcagggt aatgtcttta gttgttcagt gatgcacgaa   1380
gcactgcaca accactacac ccagaaatca ctgtcactgt caccagggaa aggatcttcc   1440
gaaacgcagg ccaactcgac cacagatgct ctgaacgttc ttctcatcat cgtggatgac   1500
ctgcgcccct ccctgggctg ttatggggat aagctggtga ggtccccaaa tattgaccaa   1560
ctggcatccc acagcctcct cttccagaat gcctttgcgc agcaagcagt gtgcgcccg    1620
agccgcgttt ctttcctcac tggcaggaga cctgacacca cccgcctgta cgacttcaac   1680
tcctactgga gggtgcacgc tggaaacttc tccaccatcc cccagtactt caaggagaat   1740
ggctatgtga ccatgtcggt gggaaaagtc tttcaccctg gatatcttc taaccatacc    1800
gatgattctc cgtatagctg gtcttttcca ccttatcatc cttcctctga agtatgaa     1860
aacactaaga catgtcgagg ccagatgga gaactccatg ccaacctgct ttgccctgtg    1920
gatgtgctgg atgttcccga gggcaccttg cctgacaaac agagcactga gcaagccata   1980
cagttgttgg aaaagatgaa aacgtcagcc agtcctttct tcctggccgt tgggtatcat   2040
aagccacaca tccccttcag ataccccaag gaatttcaga agttgtatcc cttggagaac   2100
atcaccctgg cccccgatcc cgaggtccct gatggcctac cccctgtggc ctacaacccc   2160
tggatggaca tcaggcaacg ggaagacgtc aagccttaa acatcagtgt gccgtatggt    2220
ccaattcctg tggactttca gcggaaaatc cgccagagct actttgcctc tgtgtcatat   2280
ttggatacac aggtcggccg cctcttgagt gctttggacg atcttcagct ggccaacagc   2340
accatcattg catttacctc ggatcatggg tgggctctag gtgaacatgg agaatgggcc   2400
aaatacagca ttttgatgt tgctacccat gttccctga tattctatgt tcctggaagg     2460
acggcttcac ttccggaggc aggcgagaag ctttttccctt acctcgaccc tttgattcc   2520
gcctcacagt tgatggagcc aggcaggcaa tccatggacc ttgtggaact tgtgtctctt   2580
tttcccacgc tggctggact tgcaggactg caggttccac ctcgctgccc cgttccttca   2640
tttcacgttg agctgtgcag agaaggcaag aaccttctga agcattttcg attccgtgac   2700
ttggaagaag atccgtacct ccctggtaat ccccgtgaac tgattgccta tagccagtat   2760
ccccggcctt cagacatccc tcagtggaat tctgacaagc cgagtttaaa agatataaag   2820
atcatgggct attccatacg caccatagac tataggtata ctgtgtgggt tggcttcaat   2880
cctgatgaat tctagctaa ctttttctgac atccatgcag gggaactgta ttttgtggat   2940
tctgacccat tgcaggatca caatatgtat aatgattccc aaggtggaga ccttttccag   3000
ttgttgatgc cttaagcggc cgc                                          3023
```

<210> SEQ ID NO 26
<211> LENGTH: 3011
<212> TYPE: DNA
<213> ORGANISM: Artificial Sequence
<220> FEATURE:
<223> OTHER INFORMATION: Nucleotide seuquence encoding amino acid sequence of fusion protein of the heavy-chain of humanized anti-hTfR antibody No.3 and hI2S, synthetic sequence

<400> SEQUENCE: 26

```
acgcgtgccg ccaccatggg ctggagctgg attctgctgt tcctcctgag cgtgacagca      60
ggagtgcaca gcgaggtgca actagtgcag tctggagcag aggtgaaaaa gcccggggag     120
tctctgaaga tttcctgtaa gggttctgga tacagcttta ccaactactg gctgggatgg     180
gtgcgccaga tgcccgggaa aggcctggag tggatggggg acatctaccc cggcggagac     240
taccctacat acagcgagaa gttcaaggtc caggtcacca tctcagccga caagtccatc     300
agcaccgcct acctgcagtg gagcagcctg aaggcctcgg acaccgccat gtattactgt     360
gcgagatcag caattacga cgaagtggcc tactggggcc aaggaaccct ggtcaccgtc     420
tcctcagcta gcaccaaggg cccatcggtc ttccccctgg cacctcctc caagagcacc     480
tctgggggca gcggccct gggctgcctg gtcaaggact acttcccga accggtgacg     540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacacg tgcccaccgt gcccagcacc tgaactcctg     780
ggaggtccgt cagtcttcct cttccccca aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagccgcg ggaggagcag     960
tacaacagca cgtaccgggt ggtcagcgtc ctcaccgtcc tgcaccagga ctggctgaat    1020
ggcaaggagt acaagtgcaa ggtctccaac aaagcccctcc cagccccat cgagaaaacc    1080
atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga acaactacaa gaccacgcct    1260
cccgtgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga gagcctctc cctgtctccg ggtaaaggat cttccgaaac gcaggccaac    1440
tcgaccacag atgctctgaa cgttcttctc atcatcgtgg atgacctgcg ccctccctg    1500
ggctgttatg gggataagct ggtgaggtcc ccaaatattg accaactggc atcccacagc    1560
ctcctcttcc agaatgcctt tgcgcagcaa gcagtgtgcg ccccgagccg cgtttctttc    1620
ctcactggca ggagacctga caccacccgc ctgtacgact caactcccta ctggagggtg    1680
cacgctggaa acttctccac catcccccag tacttcaagg agaatggcta tgtgaccatg    1740
tcggtgggaa aagtctttca ccctgggata tcttctaacc ataccgatga ttctccgtat    1800
agctggtctt ttccaccctta tcatccttcc tctgagaagt atgaaaacac taagacatgt    1860
cgagggccag atggagaact ccatgccaac ctgctttgcc ctgtggatgt gctggatgtt    1920
cccgagggca ccttgcctga caaacagagc actgagcaag ccatacagtt gttggaaaag    1980
atgaaaacgt cagccagtcc tttcttcctg gccgttgggt atcataagcc acacatcccc    2040
ttcagatacc ccaaggaatt tcagaagttg tatcccttgg agaacatcac cctgccccc    2100
gatcccgagg tccctgatgg cctaccccct gtggcctaca acccctggat ggacatcagg    2160
```

```
caacgggaag acgtccaagc cttaaacatc agtgtgccgt atggtccaat tcctgtggac    2220
tttcagcgga aaatccgcca gagctacttt gcctctgtgt catatttgga tacacaggtc    2280
ggccgcctct tgagtgcttt ggacgatctt cagctggcca acagcaccat cattgcattt    2340
acctcggatc atgggtgggc tctaggtgaa catggagaat gggccaaata cagcaatttt    2400
gatgttgcta cccatgttcc cctgatattc tatgttcctg gaaggacggc ttcacttccg    2460
gaggcaggcg agaagctttt cccttacctc gaccctttg attccgcctc acagttgatg     2520
gagccaggca ggcaatccat ggaccttgtg gaacttgtgt ctcttttttcc cacgctggct   2580 ggacttgcag gactgcaggt tccacctcgc tgccccgttc cttcatttca cgttgagctg    2640
tgcagagaag gcaagaacct tctgaagcat tttcgattcc gtgacttgga agaagatccg    2700
tacctccctg gtaatccccg tgaactgatt gcctatagcc agtatccccg gccttcagac    2760
atccctcagt ggaattctga caagccgagt ttaaaagata taaagatcat gggctattcc    2820
atacgcacca tagactatag gtatactgtg tgggttggct tcaatcctga tgaatttcta    2880
gctaactttt ctgacatcca tgcaggggaa ctgtattttg tggattctga cccattgcag    2940
gatcacaata tgtataatga ttcccaaggt ggagaccttt tccagttgtt gatgccttaa    3000
taagcggccg c                                                         3011

<210> SEQ ID NO 27
<211> LENGTH: 20
<212> TYPE: DNA
<213> ORGANISM: Artificial Sequence
<220> FEATURE:
<223> OTHER INFORMATION: Primer Hyg-Sfi5', synthetic sequence

<400> SEQUENCE: 27
gaggccgcct cggcctctga                                                20

<210> SEQ ID NO 28
<211> LENGTH: 29
<212> TYPE: DNA
<213> ORGANISM: Artificial Sequence
<220> FEATURE:
<223> OTHER INFORMATION: Primer Hyg-BstX3', synthetic sequence

<400> SEQUENCE: 28
aaccatcgtg atgggtgcta ttcctttgc                                      29
```